US011753615B2

(12) United States Patent
Chen et al.

(10) Patent No.: US 11,753,615 B2
(45) Date of Patent: Sep. 12, 2023

(54) **GENETICALLY ENGINEERED STRAIN OF *SACCHAROMYCES CEREVISIAE*, METHOD FOR CONSTRUCTING THE SAME AND ITS USE FOR BREWING**

(71) Applicant: Tianjin University of Science and Technology, Tianjin (CN)

(72) Inventors: Yefu Chen, Tianjin (CN); Wenqi Shi, Tianjin (CN); Guo Zhang, Tianjin (CN); Ruirui Li, Tianjin (CN); Yanfang Chen, Tianjin (CN); Huan Wang, Tianjin (CN); Chunhong Sun, Tianjin (CN); Dongguang Xiao, Tianjin (CN); Xiaole Wu, Tianjin (CN); Xuewu Guo, Tianjin (CN)

(73) Assignee: Tianjin University of Science and Technology, Tianjin (CN)

( * ) Notice: Subject to any disclaimer, the term of this patent is extended or adjusted under 35 U.S.C. 154(b) by 59 days.

(21) Appl. No.: 17/411,066

(22) Filed: Aug. 25, 2021

(65) Prior Publication Data
US 2022/0389371 A1    Dec. 8, 2022

(30) Foreign Application Priority Data
Jun. 8, 2021    (CN) .......................... 202110636049.6

(51) Int. Cl.
| | | |
|---|---|---|
| *C12N 1/18* | (2006.01) |
| *C12N 9/02* | (2006.01) |
| *C12N 9/10* | (2006.01) |
| *C12N 9/00* | (2006.01) |
| *C12R 1/865* | (2006.01) |

(52) U.S. Cl.
CPC ............. *C12N 1/18* (2013.01); *C12N 9/0008* (2013.01); *C12N 9/1029* (2013.01); *C12N 9/93* (2013.01); *C12R 2001/865* (2021.05); *C12Y 102/0101* (2013.01); *C12Y 203/01084* (2013.01); *C12Y 602/01001* (2013.01)

(58) Field of Classification Search
CPC ...... C12N 1/18; C12N 9/0008; C12N 9/1029; C12N 9/93; C12N 9/0006; C12N 15/81; C12Y 102/0101; C12Y 203/01084; C12Y 602/01001; C12Y 101/01001; C12P 7/62
See application file for complete search history.

(56) References Cited

FOREIGN PATENT DOCUMENTS

| CN | 105505807 A | * | 4/2016 |
|---|---|---|---|
| CN | 108485996 A | * | 9/2018 |

OTHER PUBLICATIONS

Cardenas et al. Engineering cofactor and transport mechanisms in *Saccharomyces cerevisiae* for enhanced acetyl-CoA and polyketide biosynthesis. Metabolic Engineering 36, (2016), 80-89. (Year: 2016).*

* cited by examiner

*Primary Examiner* — Iqbal H Chowdhury

(57) ABSTRACT

The present disclosure belongs to the field of bioengineering, and relates to breeding of industrial microorganisms, in particular to a genetically engineered strain of *Saccharomyces cerevisiae*, method for constructing the same, and its use for brewing, the genetically engineered strain of *Saccharomyces cerevisiae* heterogeneously overexpresses an acetaldehyde dehydrogenase gene ALD6, an acetyl-CoA synthase gene ACS1 and an alcohol acyltransferase gene AeAT9. The *Saccharomyces cerevisiae* strain with high yield of ethyl acetate and low yield of higher alcohols provided by the present disclosure not only maintains excellent ethanol fermentation characteristics, but also reducing the production of higher alcohols which adversely affect the comfort after drinking, which is of great significance for a well-maintained and strengthened flavor characteristics of Chinese Baijiu, an improved and stabilized quality thereof, and even a reform in the fermentation process thereof.

20 Claims, 7 Drawing Sheets

Specification includes a Sequence Listing.

SEQUENCE LISTING

```
<160> NUMBER OF SEQ ID NOS: 73

<210> SEQ ID NO 1
<211> LENGTH: 1503
<212> TYPE: DNA
<213> ORGANISM: Artificial Sequence
<220> FEATURE:
<223> OTHER INFORMATION: The sequence is synthesized

<400> SEQUENCE: 1
atgactaagc tacactttga cactgctgaa ccagtcaaga tcacacttcc aaatggtttg      60
acatacgagc aaccaaccgg tctattcatt aacaacaagt ttatgaaagc tcaagacggt     120
aagacctatc ccgtcgaaga tccttccact gaaaacaccg tttgtgaggt ctcttctgcc     180
accactgaag atgttgaata tgctatcgaa tgtgccgacc gtgctttcca cgacactgaa     240
tgggctaccc aagacccaag agaaagaggc cgtctactaa gtaagttggc tgacgaattg     300
gaaagccaaa ttgacttggt ttcttccatt gaagctttgg acaatggtaa aactttggcc     360
ttagcccgtg gggatgttac cattgcaatc aactgtctaa gagatgctgc tgcctatgcc     420
gacaaagtca acggtagaac aatcaacacc ggtgacggct acatgaactt caccaccta     480 gagccaatcg gtgtctgtgg tcaaattatt ccatggaact ttccaataat gatgttggct     540
tggaagatcg ccccagcatt ggccatgggt aacgtctgta tcttgaaacc cgctgctgtc     600
acacctttaa atgccctata ctttgcttct ttatgtaaga aggttggtat tccagctggt     660
gtcgtcaaca tcgttccagg tcctggtaga actgttggtg ctgctttgac caacgaccca     720
agaatcagaa agctggcttt taccggttct acagaagtcg gtaagagtgt tgctgtcgac     780
tcttctgaat ctaacttgaa gaaaatcact ttggaactag gtggtaagtc cgcccatttg     840
gtctttgacg atgctaacat taagaagact ttaccaaatc tagtaaacgg tattttcaag     900
aacgctggtc aaatttgttc ctctggttct agaatttacg ttcaagaagg tatttacgac     960
gaactattgg ctgctttcaa ggcttacttg gaaaccgaaa tcaaagttgg taatccattt    1020
gacaaggcta acttccaagg tgctatcact aaccgtcaac aattcgacac aattatgaac    1080
tacatcgata tcggtaagaa agaaggcgcc aagatcttaa ctggtggcga aaaagttggt    1140
gacaagggtt acttcatcag accaaccgtt ttctacgatg ttaatgaaga catgagaatt    1200
```

| | |
|---|---|
| gttaaggaag aaattttggg accagttgtc actgtcgcaa agttcaagac tttagaagaa | 1260 |
| ggtgtcgaaa tggctaacag ctctgaattc ggtctaggtt ctggtatcga aacagaatct | 1320 |
| ttgagcacag gtttgaaggt ggccaagatg ttgaaggccg gtaccgtctg atcaacaca | 1380 |
| tacaacgatt ttgactccag agttccattc ggtggtgtta agcaatctgg ttacggtaga | 1440 |
| gaaatgggtg aagaagtcta ccatgcatac actgaagtaa aagctgtcag aattaagttg | 1500 |
| taa | 1503 |

<210> SEQ ID NO 2
<211> LENGTH: 2142
<212> TYPE: DNA
<213> ORGANISM: Artificial Sequence
<220> FEATURE:
<223> OTHER INFORMATION: The sequence is synthesized

<400> SEQUENCE: 2

| | |
|---|---|
| atgtcgccct ctgccgtaca atcatcaaaa ctagaagaac agtcaagtga aattgacaag | 60 |
| ttgaaagcaa aaatgtccca gtctgccgcc actgcgcagc agaagaagga acatgagtat | 120 |
| gaacatttga cttcggtcaa gatcgtgcca caacggccca tctcagatag actgcagccc | 180 |
| gcaattgcta cccactattc tccacacttg gacgggttgc aggactatca gcgcttgcac | 240 |
| aaggagtcta ttgaagaccc tgctaagttc ttcggttcta agctaccca atttttaaac | 300 |
| tggtctaagc cattcgataa ggtgttcatc ccagacccta aacgggcag ccctccttc | 360 |
| cagaacaatg catggttcct caacggccaa ttaaacgcct gttacaactg tgttgacaga | 420 |
| catgccttga agactcctaa caagaaagcc attattttcg aaggtgacga gcctggccaa | 480 |
| ggctattcca ttacctacaa ggaactactt gaagaagttt gtcaagtggc acaagtgctg | 540 |
| acttactcta tgggcgttcg caagggcgat actgttgccg tgtacatgcc tatggtccca | 600 |
| gaagcaatca taaccttgtt ggccatttcc cgtatcggtg ccattcactc cgtagtcttt | 660 |
| gccgggtttt cttccaactc cttgagagat cgtatcaacg atgggggactc taaagttgtc | 720 |
| atcactacag atgaatccaa cagaggtggt aaagtcattg agactaaaag aattgttgat | 780 |
| gacgcgctaa gagagacccc aggcgtgaga cacgtcttgg tttatagaaa gaccaacaat | 840 |
| ccatctgttg ctttccatgc ccccagagat ttggattggg caacagaaaa gaagaaatac | 900 |
| aagacctact atccatgcac acccgttgat tctgaggatc cattattctt gttgtatacg | 960 |
| tctggttcta ctggtgcccc caagggtgtt caacattcta ccgcaggtta cttgctggga | 1020 |
| gctttgttga ccatgcgcta cacttttgac actcaccaag aagacgtttt cttcacagct | 1080 |
| ggagacattg gctggattac aggccacact tatgtggttt atggtcccctt actatatggt | 1140 |
| tgtgccactt tggtctttga agggactcct gcgtacccaa attactcccg ttattgggat | 1200 |
| attattgatg aacacaaagt cacccaattt tatgttgcgc caactgcttt gcgtttgttg | 1260 |
| aaaagagctg gtgattccta catcgaaaat cattccttaa aatctttgcg ttgcttgggt | 1320 |
| tcggtcggtg agccaattgc tgctgaagtt tgggagtggt actctgaaaa aataggtaaa | 1380 |
| aatgaaatcc ccattgtaga cacctactgg caaacagaat ctggttcgca tctggtcacc | 1440 |
| ccgctggctg gtggtgttac accaatgaaa ccgggttctg cctcattccc cttcttcggt | 1500 |
| attgatgcag ttgttcttga ccctaacact ggtgaagaac ttaacaccag ccacgcagag | 1560 |
| ggtgtccttg ccgtcaaagc tgcatggcca tcatttgcaa gaactatttg gaaaaatcat | 1620 |
| gataggtatc tagacactta tttgaaccct taccctggct actatttcac tggtgatggt | 1680 |
| gctgcaaagg ataaggatgg ttatatctgg attttgggtc gtgtagacga tgtggtgaac | 1740 |

| | |
|---|---|
| gtctctggtc accgtctgtc taccgctgaa attgaggctg ctattatcga agatccaatt | 1800 |
| gtggccgagt gtgctgttgt cggattcaac gatgacttga ctggtcaagc agttgctgca | 1860 |
| tttgtggtgt tgaaaaacaa atctagttgg tccaccgcaa cagatgatga attacaagat | 1920 |
| atcaagaagc atttggtctt tactgttaga aaagacatcg ggccatttgc cgcaccaaaa | 1980 |
| ttgatcattt tagtggatga cttgcccaag acaagatccg gcaaaattat gagacgtatt | 2040 |
| ttaagaaaaa tcctagcagg agaaagtgac caactaggcg acgttctac attgtcaaac | 2100 |
| cctggcattg ttagacatct aattgattcg gtcaagttgt aa | 2142 |

<210> SEQ ID NO 3
<211> LENGTH: 1050
<212> TYPE: DNA
<213> ORGANISM: Artificial Sequence
<220> FEATURE:
<223> OTHER INFORMATION: The sequence is synthesized

<400> SEQUENCE: 3

| | |
|---|---|
| adhatgtcta ttccagaaac tcaaaaagcc attatcttct acgaatccaa cggcaagttg | 60 |
| gagcataagg atatcccagt tccaaagcca aagcccaacg aattgttaat caacgtcaag | 120 |
| tactctggtg tctgccacac cgatttgcac gcttggcatg gtgactggcc attgccaact | 180 |
| aagttaccat tagttggtgg tcacgaaggt gccggtgtcg ttgtcggcat gggtgaaaac | 240 |
| gttaagggct ggaagatcgg tgactacgcc ggtatcaaat ggttgaacgg ttcttgtatg | 300 |
| gcctgtgaat actgtgaatt gggtaacgaa tccaactgtc ctcacgctga cttgtctggt | 360 |
| tacacccacg acggttcttt ccaagaatac gctaccgctg acgctgttca agccgctcac | 420 |
| attcctcaag gtactgactt ggctgaagtc gcgccaatct tgtgtgctgg tatcaccgta | 480 |
| tacaaggctt tgaagtctgc caacttgaga gcaggccact gggcggccat ttctggtgct | 540 |
| gctggtggtc taggttcttt ggctgttcaa tatgctaagg cgatgggtta cagagtctta | 600 |
| ggtattgatg gtggtccagg aaaggaagaa ttgtttacct cgctcggtgg tgaagtattc | 660 |
| atcgacttca ccaaagagaa ggacattgtt agcgcagtcg ttaaggctac caacggcggt | 720 |
| gcccacggta tcatcaatgt ttccgtttcc gaagccgcta tcgaagcttc taccagatac | 780 |
| tgtagggcga acggtactgt tgtcttggtt ggtttgccag ccggtgcaaa gtgctcctct | 840 |
| gatgtcttca accacgttgt caagtctatc tccattgtcg gctcttacgt ggggaacaga | 900 |
| gctgatacca gagaagcctt agatttcttt gccagaggtc tagtcaagtc tccaataaag | 960 |
| gtagttggct tatccagttt accagaaatt tacgaaaaga tggagaaggg ccaaattgct | 1020 |
| ggtagatacg ttgttgacac ttctaaataa | 1050 |

<210> SEQ ID NO 4
<211> LENGTH: 1299
<212> TYPE: DNA
<213> ORGANISM: Artificial Sequence
<220> FEATURE:
<223> OTHER INFORMATION: The sequence is synthesized

<400> SEQUENCE: 4

| | |
|---|---|
| atggcttcat ctgtcaggtt ggtcaagaag ccagtcttgg tcgctccagt tgatccaact | 60 |
| ccatcaacag ttttatcttt gtcatctttg gattcacaat tgttttttgag attccctatt | 120 |
| gaatatttgt tagtctatgc ttctccacat ggtgttgata gggctgtcac tgctgctagg | 180 |
| gtcaaagctg cattggctag gtctttggtc ccttattatc cattggctgg tagggtcaag | 240 |

```
actaggccag actctactgg attggacgtt gtctgccaag ctcaaggtgc tggattgttg    300
gaggctgtct ctgactacac agcttcagac tttcaaagag ctccaagatc tgttactgag    360
tggagaaaat tgttgttggt tgaggtcttc aaggtcgtcc ctccattggt cgttcagttg    420
acttggttgt cagacggttg cgtcgctttg ggtgttggtt tctctcactg cgtcattgac    480
ggtattggtt catcagagtt tttaaatttg tttgctgaat tggctactgg tagggcaagg    540
ttgtcagaat tccagccaaa accagtctgg gataggcact tgttaaactc tgcaggtagg    600
acaaacttgg gtactcaccc tgagtttgga agggtcccag acttgtctgg tttcgttaca    660
aggtttactc aagaaaggtt gtctccaact tctattactt tgataaaaac ttggttgaag    720
gaattaaaaa atattgctat gtctacatca cagcctggtg agttcccata cacttctttc    780
gaggtcttgt ctggtcacat atggaggtct tgggctaggt cattgaactt gccagctaag    840
caagttttaa aattgttatt ttctattaat attagaaaca gggttaagcc atctttgcca    900
gctggttact acggtaacgc tttcgtcttg ggttgcgctc agacatctgt caaggatttg    960
actgagaagg gtttgggtta ctgcgctgat ttggtcagag gtgcaaagga aagggtcggt   1020
gacgaatacg ctagggaagt tgtcgaatct gtctcttggc caaggagagc ttcaccagat   1080
tctgttggag ttttgattat ttctcaatgg tcaaggttgg gattggatag ggtcgacttc   1140
ggtttaggaa ggccagtcca ggttggacca atttgctgtg acagatattg tttgttttg    1200 ccagttaggg agtctactga gtctgtcaag gtcatggtcg ctgttccaac atctgctgtt   1260
gataggtatg aatactttat tagatctcca tactcttaa                         1299
```

<210> SEQ ID NO 5
<211> LENGTH: 846
<212> TYPE: DNA
<213> ORGANISM: Artificial Sequence
<220> FEATURE:
<223> OTHER INFORMATION: The sequence is synthesized

<400> SEQUENCE: 5

```
atggcactac gatttttcaa cgatatatct agagatgtca atggcctatt caatagggac     60
ttttttcaca ccaaccccct ctctttgaat atttcaacaa ccacggaaaa tggtgtgaat    120
tttactctga aggcgaagca gggcgtgaca gaaggcccca tccaaactag cgtagaagga    180
cggttttatg acaggaagga gggagtgtcg ctatctcaga gttggtcgaa ccagaacagg    240
ttaaatacaa gaatcgaatt tccaagata gcacctggtt ggaaaggtga tgtcaacgca     300
tttttgactc cccaatccat caagaacgcc aaatttaatt tgagctacgc ccaaaaatcg    360
tttgcagcaa gaacttctat agacatcttg caacctaagg actttgtcgg aagtgttact    420
ttgggccacc gcgggtttgt tggcggcact gacatcgcat atgacacagc tgcgggttta    480
tgtgcacgct atgctatgtc aatcgggtat cttgccagag aatattcgtt tattttgtct    540
actaacaaca ggcaatgcgc aactgcttca ttttttcaaa cgttaaccg ctatttgcaa     600 gtgggaacta aagccacttt acaatcgaag acaagttcta atatgaacat tgaatttgtt    660
accagatacg taccagattc tatttcgcaa gttaaggcaa aaattgcaga ttcaggcctg    720
actacattgt cgtacaagcg aaatttgaat aaagatattt cttgggtgt gggtatgtct    780 ttcaatgcgc tacaactgac tgaaccagtc cacaaatttg gctggtctct atcgttctcg    840
ccctga                                                              846
```

<210> SEQ ID NO 6
<211> LENGTH: 1308

<212> TYPE: DNA
<213> ORGANISM: Artificial Sequence
<220> FEATURE:
<223> OTHER INFORMATION: The sequence is synthesized

<400> SEQUENCE: 6

```
atggactaca acaagagatc ttcggtctca accgtgccta atgcagctcc cataagagtc    60
ggattcgtcg gtctcaacgc agccaaagga tgggcaatca agacacatta ccccgccata   120
ctgcaactat cgtcacaatt tcaaatcact gccttataca gtccaaaaat tgagacttct   180
attgccacca ttcagcgtct aaaattgagt aatgccactg cttttcccac tttagagtca   240
tttgcatcat cttccactat agatatgata gtgatagcta ccaagtggc cagccattat    300
gaagttgtta tgcctctctt ggaattctcc aaaaataatc cgaacctcaa gtatcttttc   360
gtagaatggg cccttgcatg ttcactagat caagccgaat ccatttataa ggctgctgct   420
gaacgtgggg ttcaaaccat catctcttta caaggtcgta aatcaccata tattttgaga   480
gcaaaagaat taatatctca aggctatatc ggcgacatta ttcgatcga gattgctgga    540
aatggcggtt ggtacggcta cgaaaggcct gttaaatcac caaatacat ctatgaaatc    600
gggaacggtg tagatctggt aaccacaaca tttggtcaca caatcgatat tttacaatac   660
atgacaagtt cgtactttc caggataaat gcaatggttt tcaataatat tccagagcaa   720
gagctgatag atgagcgtgg taaccgattg ggccagcgag tcccaaagac agtaccggat   780
catcttttat tccaaggcac attgttaaat ggcaatgttc cagtgtcatg cagtttcaaa   840
ggtggcaaac ctaccaaaaa atttaccaaa aatttggtca ttgacattca cggtaccaag   900
ggagatttga acttgaagg cgatgccggc ttcgcagaaa tttcaaatct ggtcctttac   960
tacagtggaa ctagagcaaa cgacttcccg ctagccaatg acaacaagc tcctttagac  1020
ccggggtatg atgcaggtaa agaaatcatg gaagtatatc atttacgaaa ttataatgcc  1080
attgtgggta atattcatcg actgtatcaa tctatctctg acttccactt caatacaaag  1140
aaaattcctg aattaccctc acaatttgta atgcaaggtt tcgatttcga aggctttccc  1200
acttgatgg atgctctgat attacacagg ttaatcgaga gcgtttataa aagtaacatg   1260
atgggctcca cattaaacgt tagcaatatc tcgcattata gtttataa               1308
```

<210> SEQ ID NO 7
<211> LENGTH: 1479
<212> TYPE: DNA
<213> ORGANISM: Artificial Sequence
<220> FEATURE:
<223> OTHER INFORMATION: The sequence is synthesized

<400> SEQUENCE: 7

```
tctaactgat ctatccaaaa ctgaaaatta cattcttgat taggtttatc acaggcaaat    60
gtaatttgtg gtattttgcc gttcaaaatc tgtagaattt tctcattggt cacattacaa   120
cctgaaaata ctttatctac aatcatacca ttccttataac atgtcccctt aatactagga   180
tcaggcatga acgcatcaca gacaaaatct tcttgacaaa cgtcacaatt gatccctccc   240
catccgttat cacaatgaca ggtgtcattt tgtgctctta tgggacgatc cttattaccg   300
ctttcatccg gtgatagacc gccacagagg ggcagagagc aatcatcacc tgcaaaccct   360
tctatacact cacatctacc agtgtacgaa ttgcattcag aaaactgttt gcattcaaaa   420
ataggtagca tacaattaaa acatggcggg cacgtatcat tgcccttatc ttgtgcagtt   480
agacgcgaat ttttcgaaga agtaccttca aagaatgggg tctcatcttg ttttgcaagt   540
```

```
accactgagc aggataataa tagaaatgat aatatactat agtagagata acgtcgatga      600
cttcccatac tgtaattgct tttagttgtg tattttagt gtgcaagttt ctgtaaatcg       660
attaattttt ttttctttcc tcttttatt aaccttaatt tttattttag attcctgact      720
tcaactcaag acgcacagat attataacat ctgcacaata ggcatttgca agaattactc      780
gtgagtaagg aaagagtgag gaactatcgc atacctgcat ttaaagatgc cgatttgggc     840
gcgaatcctt tattttggct tcaccctcat actattatca gggccagaaa aaggaagtgt     900
ttccctcctt cttgaattga tgttaccctc ataaagcacg tggcctctta tcgagaaaga    960
aattaccgtc gctcgtgatt tgtttgcaaa aagaacaaaa ctgaaaaaac ccagacacgc    1020
tcgacttcct gtcttcctat tgattgcagc ttccaatttc gtcacacaac aaggtcctag    1080
cgacggctca caggttttgt aacaagcaat cgaaggttct ggaatggcgg gaaagggttt    1140
agtaccacat gctatgatgc ccactgtgat ctccagagca aagttcgttc gatcgtactg    1200
ttactctctc tctttcaaac agaattgtcc gaatcgtgtg acaacaacag cctgttctca    1260
cacactcttt tcttctaacc aagggggtgg tttagtttag tagaacctcg tgaaacttac    1320
atttacatat atataaactt gcataaattg gtcaatgcaa gaaatacata tttggtcttt    1380
tctaattcgt agtttttcaa gttcttagat gctttcttt tctcttttt acagatcatc      1440 aaggaagtaa ttatctactt tttacaacaa atataaaac                            1479

<210> SEQ ID NO 8
<211> LENGTH: 599
<212> TYPE: DNA
<213> ORGANISM: Artificial Sequence
<220> FEATURE:
<223> OTHER INFORMATION: The sequence is synthesized

<400> SEQUENCE: 8
actagttttc ttctttcctc ctcttcttg aactgcttcc aaattctgtc tttaagtcca       60
tcacatggtg ttttatggga ttttgtatta ttacggtgtt cggttttctt ttgggtattg    120
agcttttatt ttggtcttaa tttttttttt tcttttcaa accatggact ttattataat     180
taatctacga caacttttaa tgattatttc tttcttcaaa tatacacgta tgtattattt    240 cttttttacta tattcttaac tctttattcc tgctcagaca acgtttcaac caacgttaat   300
atttcgttct tgtaattaat caattgggct attaagggaa tacaacctt gaaacttgtc    360 tgcgattgtc tcaatgaaga aggaacggac agtactccac caaacatcaa aattgggtcg    420
tagtcttgtt taagtttgtg actctgagtt ttttgctttt ctggcttcgt tcctttttt     480 ctctgagtca atttattatc ttcttcctct ttcttttctt gcttatcttg agcttttctt    540
ttgacgattt cgacaactac cttggagttt ttttcttcca ctgttgccat tagttgacc    599

<210> SEQ ID NO 9
<211> LENGTH: 1001
<212> TYPE: DNA
<213> ORGANISM: Artificial Sequence
<220> FEATURE:
<223> OTHER INFORMATION: The sequence is synthesized

<400> SEQUENCE: 9
cttcatcggt atcttcgcta tattcttttt agtcgaattt gcggggagaa gatggatcta      60
tgctaaacta aataggcatt tgaaaaacga cgacgagtta cacgacatat cgccatcttt     120
aaatgagcaa ccacactggg aacctcataga ggacgggtct cgctggagta aattttcaa    180 cgggataatt aagacgacaa gaaggttcac gaaatcttta atgaggtctt tagtcagagg    240
```

-continued

```
caggaacagc cgtcaagggg gcataagact acggtcatcc ccatctgcct cttcgtccag    300
ccttgccaac agggagttct tcagagacat ggaggctcaa aacgaaatta ttgacagcct    360
agacatcaat agtcatacaa cagaaagcga ccacccaact ttggctgata atagcgtata    420
aacaatgcat actttgtacg ttcaaaatac aatgcagtag atatatttat gcatattaca    480
tataatacat atcacatagg aagcaacagg cgcgttggac ttttaatttt cgaggaccgc    540
gaatccttac atcacaccca atcccccaca agtgatcccc cacacaccat agcttcaaaa    600
tgtttctact ccttttttac tcttccagat tttctcggac tccgcgcatc gccgtaccac    660
ttcaaaacac ccaagcacag catactaaat ttcccctctt tcttcctcta gggtgtcgtt    720
aattacccgt actaaaggtt tggaaaagaa aaagagacc gcctcgtttc ttttcttcg     780 tcgaaaaagg caataaaaat ttttatcacg tttcttttc ttgaaaattt ttttttttga    840 ttttttctc tttcgatgac ctcccattga tatttaagtt aataaacggt cttcaatttc     900
tcaagtttca gtttcatttt tcttgttcta ttacaacttt ttttacttct tgctcattag    960
aaagaaagca tagcaatcta atctaagttt taattacaaa a                      1001
```

<210> SEQ ID NO 10
<211> LENGTH: 258
<212> TYPE: DNA
<213> ORGANISM: Artificial Sequence
<220> FEATURE:
<223> OTHER INFORMATION: The sequence is synthesized

<400> SEQUENCE: 10

```
cgatagatca attttttct ttctctttc cccatccttt acgctaaaat aatagtttat      60 tttattttt gaatatttt tatttatata cgtatatata gactattatt tatcttttaa     120
tgattattaa gatttttatt aaaaaaaaat tcgctcctct tttaatgcct ttatgcagtt    180 ttttttccc attcgatatt tctatgttcg ggttcagcgt atttaagtt taataactcg      240 aaaattctgc gttcgtta                                                  258
```

<210> SEQ ID NO 11
<211> LENGTH: 418
<212> TYPE: DNA
<213> ORGANISM: Artificial Sequence
<220> FEATURE:
<223> OTHER INFORMATION: The sequence is synthesized

<400> SEQUENCE: 11

```
acttctcgta ggaacaattt cgggcccctg cgtgttcttc tgaggttcat ctttttacatt    60 tgcttctgct ggataatttt cagaggcaac aaggaaaaat tagatggcaa aaagtcgtct   120
ttcaaggaaa aatccccacc atctttcgag atcccctgta acttattggc aactgaaaga    180
atgaaaagga ggaaaataca aaatatacta gaactgaaaa aaaaaaagta taaatagaga    240
cgatatatgc caatacttca caatgttcga atctattctt catttgcagc tattgtaaaa    300
taataaaaca tcaagaacaa acaagctcaa cttgtctttt ctaagaacaa agaataaaca    360
caaaaacaaa aagtttttt aatttttaatc aaaaaatgtc acaagacgct gctattgc     418
```

<210> SEQ ID NO 12
<211> LENGTH: 717
<212> TYPE: DNA
<213> ORGANISM: Artificial Sequence
<220> FEATURE:
<223> OTHER INFORMATION: The sequence is synthesized

```
<400> SEQUENCE: 12
atggattacg agaagtttct gttatttggg gattccatta ctgaatttgc ttttaatact      60
aggcccattg aagatggcaa agatcagtat gctcttggag ccgcattagt caacgaatat     120
acgagaaaaa tggatattct tcaaagaggg ttcaaagggt acacttctag atgggcgttg     180
aaaatacttc ctgagatttt aaagcatgaa tccaatattg tcatggccac aatattttg      240 ggtgccaacg atgcatgctc agcaggtccc caaagtgtcc ccctcccga  atttatcgat     300 aatattcgtc aaatggtatc tttgatgaag tcttaccata tccgtcctat tataatagga    360
ccggggctag tagatagaga gaagtgggaa aaagaaaaat ctgaagaaat agctctcgga    420
tacttccgta ccaacgagaa ctttgccatt tattccgatg ccttagcaaa actagccaat    480
gaggaaaaag ttcccttcgt ggctttgaat aaggcgtttc aacaggaagg tggtgatgct    540
tggcaacaac tgctaacaga tggactgcac ttttccggaa aagggtacaa aatttttcat    600
gacgaattat tgaaggtcat tgagacattc taccccaat  atcatccaa  aaacatgcag    660 tacaaactga agattggag  agatgtgcta gatgatggat ctaacataat gtcttga       717

<210> SEQ ID NO 13
<211> LENGTH: 19
<212> TYPE: DNA
<213> ORGANISM: Artificial Sequence
<220> FEATURE:
<223> OTHER INFORMATION: The sequence is synthesized

<400> SEQUENCE: 13
ggttggcctc tacttactc                                                  19

<210> SEQ ID NO 14
<211> LENGTH: 46
<212> TYPE: DNA
<213> ORGANISM: Artificial Sequence
<220> FEATURE:
<223> OTHER INFORMATION: The sequence is synthesized

<400> SEQUENCE: 14
gaatatagcg aagataccga tgaaggacgg gagtggaaag aacggg                    46

<210> SEQ ID NO 15
<211> LENGTH: 44
<212> TYPE: DNA
<213> ORGANISM: Artificial Sequence
<220> FEATURE:
<223> OTHER INFORMATION: The sequence is synthesized

<400> SEQUENCE: 15
tatcagatcc actagtggcc tatgcgcatc ttgccctgtg cttg                      44

<210> SEQ ID NO 16
<211> LENGTH: 18
<212> TYPE: DNA
<213> ORGANISM: Artificial Sequence
<220> FEATURE:
<223> OTHER INFORMATION: The sequence is synthesized

<400> SEQUENCE: 16
ccatgctacc ttccatgg                                                   18

<210> SEQ ID NO 17
<211> LENGTH: 43
<212> TYPE: DNA
<213> ORGANISM: Artificial Sequence
```

```
<220> FEATURE:
<223> OTHER INFORMATION: The sequence is synthesized

<400> SEQUENCE: 17
gtttcccgtt ctttccactc ccgtccttca tcggtatctt cgc                         43

<210> SEQ ID NO 18
<211> LENGTH: 44
<212> TYPE: DNA
<213> ORGANISM: Artificial Sequence
<220> FEATURE:
<223> OTHER INFORMATION: The sequence is synthesized

<400> SEQUENCE: 18
atgattgtac ggcagagggc gacattttg taattaaaac ttag                         44

<210> SEQ ID NO 19
<211> LENGTH: 43
<212> TYPE: DNA
<213> ORGANISM: Artificial Sequence
<220> FEATURE:
<223> OTHER INFORMATION: The sequence is synthesized

<400> SEQUENCE: 19
tctaatctaa gttttaatta caaaaatgtc gccctctgcc gta                         43

<210> SEQ ID NO 20
<211> LENGTH: 50
<212> TYPE: DNA
<213> ORGANISM: Artificial Sequence
<220> FEATURE:
<223> OTHER INFORMATION: The sequence is synthesized

<400> SEQUENCE: 20
gagaaaagaa aaaattgat ctatcgttac aacttgaccg aatcaattag                   50

<210> SEQ ID NO 21
<211> LENGTH: 50
<212> TYPE: DNA
<213> ORGANISM: Artificial Sequence
<220> FEATURE:
<223> OTHER INFORMATION: The sequence is synthesized

<400> SEQUENCE: 21
ctaattgatt cggtcaagtt gtaacgatag atcaattttt tcttttctc                   50

<210> SEQ ID NO 22
<211> LENGTH: 45
<212> TYPE: DNA
<213> ORGANISM: Artificial Sequence
<220> FEATURE:
<223> OTHER INFORMATION: The sequence is synthesized

<400> SEQUENCE: 22
cagttttgga tagatcagtt agataacgaa cgcagaattt tcgag                       45

<210> SEQ ID NO 23
<211> LENGTH: 45
<212> TYPE: DNA
<213> ORGANISM: Artificial Sequence
<220> FEATURE:
<223> OTHER INFORMATION: The sequence is synthesized

<400> SEQUENCE: 23
ctcgaaaatt ctgcgttcgt tatctaactg atctatccaa aactg                       45
```

<210> SEQ ID NO 24
<211> LENGTH: 50
<212> TYPE: DNA
<213> ORGANISM: Artificial Sequence
<220> FEATURE:
<223> OTHER INFORMATION: The sequence is synthesized

<400> SEQUENCE: 24
cagcagtgtc aaagtgtagc ttagtcatgt tttatatttg ttgtaaaaag        50

<210> SEQ ID NO 25
<211> LENGTH: 50
<212> TYPE: DNA
<213> ORGANISM: Artificial Sequence
<220> FEATURE:
<223> OTHER INFORMATION: The sequence is synthesized

<400> SEQUENCE: 25 cttttacaa caaatataaa acatgactaa gctacacttt gacactgctg        50

<210> SEQ ID NO 26
<211> LENGTH: 42
<212> TYPE: DNA
<213> ORGANISM: Artificial Sequence
<220> FEATURE:
<223> OTHER INFORMATION: The sequence is synthesized

<400> SEQUENCE: 26
ggaggaaaga agaaaactag tttacaactt aattctgaca gc        42

<210> SEQ ID NO 27
<211> LENGTH: 42
<212> TYPE: DNA
<213> ORGANISM: Artificial Sequence
<220> FEATURE:
<223> OTHER INFORMATION: The sequence is synthesized

<400> SEQUENCE: 27
gctgtcagaa ttaagttgta aactagtttt cttctttcct cc        42

<210> SEQ ID NO 28
<211> LENGTH: 43
<212> TYPE: DNA
<213> ORGANISM: Artificial Sequence
<220> FEATURE:
<223> OTHER INFORMATION: The sequence is synthesized

<400> SEQUENCE: 28
ggaggaaaga agaaaactag tgttttatat ttgttgtaaa aag        43

<210> SEQ ID NO 29
<211> LENGTH: 43
<212> TYPE: DNA
<213> ORGANISM: Artificial Sequence
<220> FEATURE:
<223> OTHER INFORMATION: The sequence is synthesized

<400> SEQUENCE: 29 cttttacaa caaatataaa acactagttt cttctttcc tcc        43

<210> SEQ ID NO 30
<211> LENGTH: 40
<212> TYPE: DNA
<213> ORGANISM: Artificial Sequence
<220> FEATURE:
<223> OTHER INFORMATION: The sequence is synthesized

<400> SEQUENCE: 30
cctgacagat gaagccatgt tttatatttg ttgtaaaaag        40

<210> SEQ ID NO 31
<211> LENGTH: 40
<212> TYPE: DNA
<213> ORGANISM: Artificial Sequence
<220> FEATURE:
<223> OTHER INFORMATION: The sequence is synthesized

<400> SEQUENCE: 31 cttttacaa caaatataaa acatggcttc atctgtcagg         40

<210> SEQ ID NO 32
<211> LENGTH: 45
<212> TYPE: DNA
<213> ORGANISM: Artificial Sequence
<220> FEATURE:
<223> OTHER INFORMATION: The sequence is synthesized

<400> SEQUENCE: 32
gagaaaagaa aaaaattgat ctatcgttaa gagtatggag atcta  45

<210> SEQ ID NO 33
<211> LENGTH: 45
<212> TYPE: DNA
<213> ORGANISM: Artificial Sequence
<220> FEATURE:
<223> OTHER INFORMATION: The sequence is synthesized

<400> SEQUENCE: 33
tagatctcca tactcttaac gatagatcaa ttttttcct ttctc  45

<210> SEQ ID NO 34
<211> LENGTH: 39
<212> TYPE: DNA
<213> ORGANISM: Artificial Sequence
<220> FEATURE:
<223> OTHER INFORMATION: The sequence is synthesized

<400> SEQUENCE: 34
gcgtacgaag cttcagctgt aacgaacgca gaattttcg        39

<210> SEQ ID NO 35
<211> LENGTH: 39
<212> TYPE: DNA
<213> ORGANISM: Artificial Sequence
<220> FEATURE:
<223> OTHER INFORMATION: The sequence is synthesized

<400> SEQUENCE: 35
cgaaaattct gcgttcgtta cagctgaagc ttcgtacgc        39

<210> SEQ ID NO 36
<211> LENGTH: 50
<212> TYPE: DNA
<213> ORGANISM: Artificial Sequence
<220> FEATURE:
<223> OTHER INFORMATION: The sequence is synthesized

<400> SEQUENCE: 36
ggccaagcac agggcaagat gctttaaagc atcttgccct gtgcttggcc    50

<210> SEQ ID NO 37

```
<211> LENGTH: 18
<212> TYPE: DNA
<213> ORGANISM: Artificial Sequence
<220> FEATURE:
<223> OTHER INFORMATION: The sequence is synthesized

<400> SEQUENCE: 37
ctctccacca ctagtacc                                                        18

<210> SEQ ID NO 38
<211> LENGTH: 40
<212> TYPE: DNA
<213> ORGANISM: Artificial Sequence
<220> FEATURE:
<223> OTHER INFORMATION: The sequence is synthesized

<400> SEQUENCE: 38
aaattgttcc tacgagaagt atttggtcac agtttaagcg                                40

<210> SEQ ID NO 39
<211> LENGTH: 39
<212> TYPE: DNA
<213> ORGANISM: Artificial Sequence
<220> FEATURE:
<223> OTHER INFORMATION: The sequence is synthesized

<400> SEQUENCE: 39
cagatccact agtggcctat gcgatgtgct agatgatgg                                 39

<210> SEQ ID NO 40
<211> LENGTH: 19
<212> TYPE: DNA
<213> ORGANISM: Artificial Sequence
<220> FEATURE:
<223> OTHER INFORMATION: The sequence is synthesized

<400> SEQUENCE: 40
ctcctggtcc catatgtgc                                                       19

<210> SEQ ID NO 41
<211> LENGTH: 40
<212> TYPE: DNA
<213> ORGANISM: Artificial Sequence
<220> FEATURE:
<223> OTHER INFORMATION: The sequence is synthesized

<400> SEQUENCE: 41
cgcttaaact gtgaccaaat acttctcgta ggaacaattt                                40

<210> SEQ ID NO 42
<211> LENGTH: 42
<212> TYPE: DNA
<213> ORGANISM: Artificial Sequence
<220> FEATURE:
<223> OTHER INFORMATION: The sequence is synthesized

<400> SEQUENCE: 42
gagtttctgg aatagacatg caatagcagc gtcttgtgac at                             42

<210> SEQ ID NO 43
<211> LENGTH: 42
<212> TYPE: DNA
<213> ORGANISM: Artificial Sequence
<220> FEATURE:
<223> OTHER INFORMATION: The sequence is synthesized

<400> SEQUENCE: 43
```

```
atgtcacaag acgctgctat tgcatgtcta ttccagaaac tc                          42
```

<210> SEQ ID NO 44
<211> LENGTH: 41
<212> TYPE: DNA
<213> ORGANISM: Artificial Sequence
<220> FEATURE:
<223> OTHER INFORMATION: The sequence is synthesized

<400> SEQUENCE: 44

```
gaaaaaaatt gatctatcgt tatttagaag tgtcaacaac g                           41
```

<210> SEQ ID NO 45
<211> LENGTH: 41
<212> TYPE: DNA
<213> ORGANISM: Artificial Sequence
<220> FEATURE:
<223> OTHER INFORMATION: The sequence is synthesized

<400> SEQUENCE: 45

```
cgttgttgac acttctaaat aacgatagat caatttttt c                            41
```

<210> SEQ ID NO 46
<211> LENGTH: 39
<212> TYPE: DNA
<213> ORGANISM: Artificial Sequence
<220> FEATURE:
<223> OTHER INFORMATION: The sequence is synthesized

<400> SEQUENCE: 46

```
ccatcatcta gcacatcgca taggccacta gtggatctg                              39
```

<210> SEQ ID NO 47
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 47

```
ctgatcttgt cttactcgtt c                                                 21
```

<210> SEQ ID NO 48
<211> LENGTH: 43
<212> TYPE: DNA
<213> ORGANISM: Artificial Sequence
<220> FEATURE:
<223> OTHER INFORMATION: The sequence is synthesized

<400> SEQUENCE: 48

```
gcgtacgaag cttcagctgc gtaggtaatt tctaacactt tcc                         43
```

<210> SEQ ID NO 49
<211> LENGTH: 41
<212> TYPE: DNA
<213> ORGANISM: Artificial Sequence
<220> FEATURE:
<223> OTHER INFORMATION: The sequence is synthesized

<400> SEQUENCE: 49

```
cagatccact agtggcctat gcgggtgtgg gtatgtcttt c                           41
```

<210> SEQ ID NO 50
<211> LENGTH: 20
<212> TYPE: DNA

```
<213> ORGANISM: Artificial Sequence
<220> FEATURE:
<223> OTHER INFORMATION: The sequence is synthesized

<400> SEQUENCE: 50
cttaaaaccg aagtcttcgg                                                    20

<210> SEQ ID NO 51
<211> LENGTH: 43
<212> TYPE: DNA
<213> ORGANISM: Artificial Sequence
<220> FEATURE:
<223> OTHER INFORMATION: The sequence is synthesized

<400> SEQUENCE: 51
ggaaagtgtt agaaattacc tacgcagctg aagcttcgta cgc                          43

<210> SEQ ID NO 52
<211> LENGTH: 41
<212> TYPE: DNA
<213> ORGANISM: Artificial Sequence
<220> FEATURE:
<223> OTHER INFORMATION: The sequence is synthesized

<400> SEQUENCE: 52
gaaagacata cccacacccg cataggccac tagtggatct g                            41

<210> SEQ ID NO 53
<211> LENGTH: 28
<212> TYPE: DNA
<213> ORGANISM: Artificial Sequence
<220> FEATURE:
<223> OTHER INFORMATION: The sequence is synthesized

<400> SEQUENCE: 53
atcgtcgacc ccacacacca tagcttca                                           28

<210> SEQ ID NO 54
<211> LENGTH: 29
<212> TYPE: DNA
<213> ORGANISM: Artificial Sequence
<220> FEATURE:
<223> OTHER INFORMATION: The sequence is synthesized

<400> SEQUENCE: 54
gcggtcgaca gcttgcaaat taaagcctt                                          29

<210> SEQ ID NO 55
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 55
ctgctggtct tctggtctgt                                                    20

<210> SEQ ID NO 56
<211> LENGTH: 19
<212> TYPE: DNA
<213> ORGANISM: Artificial Sequence
<220> FEATURE:
<223> OTHER INFORMATION: The sequence is synthesized

<400> SEQUENCE: 56
ttttgtaatt aaaacttag                                                     19
```

<210> SEQ ID NO 57
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 57
atgtcgccct ctgccgtaca atc                                              23

<210> SEQ ID NO 58
<211> LENGTH: 22
<212> TYPE: DNA
<213> ORGANISM: Artificial Sequence
<220> FEATURE:
<223> OTHER INFORMATION: The sequence is synthesized

<400> SEQUENCE: 58
cgatttacag aaacttgcac ac                                               22

<210> SEQ ID NO 59
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 59
tcaccacctt agagccaatc                                                  20

<210> SEQ ID NO 60
<211> LENGTH: 19
<212> TYPE: DNA
<213> ORGANISM: Artificial Sequence
<220> FEATURE:
<223> OTHER INFORMATION: The sequence is synthesized

<400> SEQUENCE: 60
cgatagatca atttttttc                                                   19

<210> SEQ ID NO 61
<211> LENGTH: 22
<212> TYPE: DNA
<213> ORGANISM: Artificial Sequence
<220> FEATURE:
<223> OTHER INFORMATION: The sequence is synthesized

<400> SEQUENCE: 61
gttattcatt cgtgattgcg cc                                               22

<210> SEQ ID NO 62
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 62
cagactaaac tggctgacgg                                                  20

<210> SEQ ID NO 63
<211> LENGTH: 20
<212> TYPE: DNA
<213> ORGANISM: Artificial Sequence
<220> FEATURE:

<223> OTHER INFORMATION: The sequence is synthesized

<400> SEQUENCE: 63
tgcccacaga ctaagttcca                                            20

<210> SEQ ID NO 64
<211> LENGTH: 24
<212> TYPE: DNA
<213> ORGANISM: Artificial Sequence
<220> FEATURE:
<223> OTHER INFORMATION: The sequence is synthesized

<400> SEQUENCE: 64
gcatcgtacg caggatggaa attg                                       24

<210> SEQ ID NO 65
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 65
gcaatagcag cgtcttgtga cat                                        23

<210> SEQ ID NO 66
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 66
acttctcgta ggaacaattt                                            20

<210> SEQ ID NO 67
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 67
taacgaacgc agaattttcg                                            20

<210> SEQ ID NO 68
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 68
cagactaaac tggctgacgg                                            20

<210> SEQ ID NO 69
<211> LENGTH: 22
<212> TYPE: DNA
<213> ORGANISM: Artificial Sequence
<220> FEATURE:
<223> OTHER INFORMATION: The sequence is synthesized

<400> SEQUENCE: 69
caagccatag ctgcttctgg ag                                         22

```
<210> SEQ ID NO 70
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 70
gatgtgtata tgttcatgcg                                                    20

<210> SEQ ID NO 71
<211> LENGTH: 22
<212> TYPE: DNA
<213> ORGANISM: Artificial Sequence
<220> FEATURE:
<223> OTHER INFORMATION: The sequence is synthesized

<400> SEQUENCE: 71
gttattcatt cgtgattgcg cc                                                 22

<210> SEQ ID NO 72
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 72
cagactaaac tggctgacgg                                                    20

<210> SEQ ID NO 73
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 73
cttactacca gaggcagcaa c                                                  21
```

GENETICALLY ENGINEERED STRAIN OF *SACCHAROMYCES CEREVISIAE*, METHOD FOR CONSTRUCTING THE SAME AND ITS USE FOR BREWING

CROSS REFERENCE TO THE RELATED APPLICATION

This application is based upon and claims the priority of the Chinese patent application filed on Jun. 8, 2021, with the application number of CN202110636049.6, the entire contents of which are incorporated herein by reference.

REFERENCE TO SEQUENCE LISTING

A Sequence Listing is submitted as an ASCII formatted text file via EFS-Web, with a file name of "Sequence_Listing_RSMK-21001-USPT.TXT", a creation date of Aug. 24, 2021, and a size of 30,790 bytes. The Sequence Listing filed via EFS-Web is part of the specification and is incorporated in its entirety by reference herein.

FIELD OF TECHNOLOGY

The present disclosure belongs to the field of bioengineering and relates to breeding of industrial microorganisms, in particular to a genetically engineered strain of *Saccharomyces cerevisiae*, method for constructing the same, and its use for brewing.

BACKGROUND

Chinese Baijiu is a liquor unique to China, popular among consumers as one of the seven major distilled spirits in the world. The trace ingredients in Chinese Baijiu are the main factors that determine the quality of the liquor, among which esters are the most important flavor compounds, providing for a pleasant fruity aroma of the liquor. Ethyl acetate is a main fragrance of light-flavor Baijiu with a higher content among the various flavor esters in the liquor. How to effectively improve the yield of ethyl acetate has always been the focus of studies in alcoholic beverage.

Inclusion of pure-bred *Saccharomyces cerevisiae* to Baijiu fermentation leads to a short fermentation period and a high alcohol yield from raw materials, but also a poor quality in the flavor of the finished liquor because of the extremely low capacity of *Saccharomyces cerevisiae* for the yield of ester-aroma substances. Ethyl acetate of a higher concentration in light-flavor Baijiu is produced from naturally trapped or enhanced addition of ester-producing yeasts. Guangsen Fan et al. Screened an ester-producing yeast with high yield of ethyl acetate, *Wickerhamomyces anomalus*, from Gujing Gong Daqu, the ethyl acetate-yield of which could be as high as 16.92 g/L under optimized fermentation conditions. However, with an ethanol fermentation efficiency of less than one third of that of *Saccharomyces cerevisiae*, the non-*saccharomyces* yeasts have a serious impact on the alcohol yield from raw materials, resulting in the production of premium Baijiu with high consumption of grains, long production period, low efficiency and high cost. Therefore, constructing a new *Saccharomyces cerevisiae* strain with high yield of ethyl acetate, which maintains excellent ethanol fermentation characteristics while producing a basic ester fragrant substance, ethyl acetate, during fermentation, which is of great significance for a well-maintained and strengthened flavor characteristics of Chinese Baijiu, an improved and stabilized quality, and even a reform in the fermentation process thereof.

During the process of Baijiu brewing, *Saccharomyces cerevisiae* absorbs the free amino acids in the raw materials, the amino group of which is used to synthesize the protein required for the growth and reproduction of the yeast itself, and the remaining (α-keto acid) forms higher alcohols through irreversible reactions. Higher alcohols of a too high concentration bring adverse flavor to Baijiu. For example, at a concentration close to the threshold, β-phenylethanol gives a fat-like sourness, isoamyl alcohol (active pentanol) gives a fusel oil flavor, n-propanol gives an ether odor and bitterness, and n-butanol gives a solvent-like flavor, bitterness, and a slight jasmine fragrance. In addition, an excessive amount of higher alcohols can cause certain damage to the body of the drinkers, such as headaches among other symptoms of alcohol poisoning after drinking. Currently the issue of excessively high content of higher alcohols in Baijiu exists in many domestic distilleries, especially in summer, the peak production season under high temperature, which requires to a certain extent a shortened fermentation; moreover, some companies, especially those small and medium-sized distilleries increase the proportion of auxiliary materials to reduce costs, resulting in higher alcohols accumulating in Baijiu to a level that is much higher than normal. Therefore, inspection and control should be strengthened, and measures should be taken in a timely manner to restrict the level of higher alcohols in a reasonable range.

In short, constructing a *Saccharomyces cerevisiae* strain with high yield of ethyl acetate and low yield of higher alcohols, which not only maintains excellent ethanol fermentation characteristics, but also produces a basic ester fragrant substance, ethyl acetate, during fermentation, while reducing the production of higher alcohols which adversely affect the comfort after drinking, which is of great significance to a well-maintained and strengthened flavor characteristics of Chinese Baijiu, an improved and stabilized quality, and even a reform in the fermentation process thereof.

SUMMARY

The present disclosure provides a genetically engineered strain of *Saccharomyces cerevisiae*, method for constructing the same, and its use for brewing. The *Saccharomyces cerevisiae* strain with high yield of ethyl acetate and low yield of higher alcohols provided by the present disclosure not only maintains excellent ethanol fermentation characteristics, but also produces a basic ester fragrant substance, ethyl acetate, during fermentation, while reducing the production of higher alcohols which adversely affect the comfort after drinking, which is of great significance to a well-maintained and strengthened flavor characteristics of Chinese Baijiu, an improved and stabilized quality thereof, and even a reform in the fermentation process thereof.

In the first aspect, the present disclosure provides a genetically engineered strain of *Saccharomyces cerevisiae*, the engineered strain heterogeneously overexpresses an acetaldehyde dehydrogenase gene ALD6, an acetyl-CoA synthase gene ACS1 and an alcohol acyltransferase gene AeAT9.

In the second aspect, a method for constructing the above genetically engineered strain of *Saccharomyces cerevisiae* is provided, comprising: introducing into *Saccharomyces cerevisiae* the aldehyde dehydrogenase gene ALD6, the acetyl-CoA synthase gene ACS1, the alcohol acyltransferase gene AeAT9 and optionally the alcohol dehydrogenase gene ADH2; and optionally inactivating or knocking out the porin gene POR2 responsible for transporting cytosolic pyruvate into the mitochondria;

In the third aspect, the present disclosure provides a use of the genetically engineered strain of *Saccharomyces cerevisiae* for brewing.

Beneficial Effects:

1. The *Saccharomyces cerevisiae* strain constructed in the present disclosure was used for fermentation of corn hydrolysate, and the results showed that: while the original strain has a low capacity of ethyl acetate production with ethyl acetate yield of 6.34 mg/L, the yield of ethyl acetate increased to 1374.52 mg/L (216.8 times higher than that of the original strain) after the simultaneously integration and overexpression of the acetaldehyde dehydrogenase gene ALD6, the acetyl-CoA synthase gene ACS1 and the alcohol acyltransferase gene AeAT9; the yield of ethyl acetate increased to 1425.85 mg/L (224.9 times higher than that of the original strain) after a further integration and overexpression of the alcohol dehydrogenase gene ADH2; and the final yield of ethyl acetate increased to 1651.89 mg/L (260.55 times higher than that of the original strain) after a further knockout of the gene POR2. In addition, the yield of isoamyl acetate was very low, and no isobutyl acetate was detected. Meanwhile, the content of higher alcohols, especially isoamyl alcohol, dropped significantly, down by 66.45% compared with the control.

2. The *Saccharomyces cerevisiae* strain PGA2AeΔPor2 constructed in the present disclosure was used for fermentation of Chi Xiang Xing Baijiu (Zhaijiu), and the highest yield of ethyl acetate, 534.43 mg/L, was obtained on day 9 of the fermentation, 8.89 times that of the blank control, and 1.55 times that of the MY-15 strain. After 15 days of fermentation, the concentrations of various higher alcohols in the PGA2AeΔPor2 fermentation system all reduced to their lowest values, i.e., 109.49, 136.18 and 38.7 mg/L for isobutanol, isoamyl alcohol and n-propanol respectively, which dropped by 43.23%, 29.39% and 19.26%, respectively compared with the control, and 12.11%, 12.89% and 18.39% respectively compared with that of the MY-15 strain. In general, the *Saccharomyces cerevisiae* strain PGA2AeΔPor2 constructed in the present disclosure not only features high yield of ethyl acetate, but has the capacity of reducing higher alcohols.

3. The *Saccharomyces cerevisiae* strain PGA2AeΔPor2 constructed in the present disclosure was used for a second fermentation of light-flavor Baijiu, and demonstrated again a high capacity of ethyl acetate synthesis with an ethyl acetate concentration of 305.30 mg/L, which was 11.93 times that of the ADY strain and 2.05 times that of the MY-15 strain. Moreover, the MY-15 and ADY strains showed an increased concentrations of various higher alcohols and total higher alcohols, except for the concentration of isoamyl alcohol which slightly decreased, while the strain PGA2AeΔPor2 constructed in the present disclosure showed a more obvious effect on the reduction of higher alcohols. In addition, the PGA2AeΔPor2 strain maintains a relatively high ethanol fermentation characteristic while improving the synthesis of ethyl acetate and reducing the yield of higher alcohols.

4. There were no significant difference in the levels of alcohol and residual sugars between the recombinant strain and the original strain in the present disclosure; the knockout of the coding gene Gal80 of a transcription regulator, gene IAH1 and gene POR2, and the operations related to the overexpression of acetaldehyde dehydrogenase gene ALD6, acetyl-CoA synthase gene ACS1, alcohol dehydrogenase gene ADH2, and the heterogeneous overexpression of alcohol acyltransferase gene AeAT9, had no adverse impact on the essential fermentation performance of the strain.

5. The strain provided by the present disclosure not only maintains an essential ethanol fermentation characteristic, but maintains high yield of ethyl acetate while enduring the high acidity during Baijiu fermentation, and can significantly reduce the production of higher alcohols. The overexpression genes related to the construction of the strain are preferably derived from *Saccharomyces cerevisiae* itself or fruits, and the strain does not contain any foreign genes such as selectable markers. The strain has broad application prospects in the fermentation and production of light-flavour Baijiu and other alcoholic beverages.

(b) M is marker; lane 1 and 2 are fragments verified by PCR amplification using ACS1-S/PGK1$_P$-X as primer, and genome of the original strain α as template for lane 1 and genome of the recombinant strain PGAe as template for lane 2;

(c) M is marker; lane 1 and 2 are fragments verified by PCR amplification using ALD6-S/PGK1$_P$-D as primer, and genome of the original strain α as template for lane 1 and genome of the recombinant strain PGAe as template for lane 2;

(d) M is marker; lane 1 and 2 are fragments verified by PCR amplification using PGK1$_T$-U/KAN-X as primer, and genome of the original strain α as template for lane 1 and genome of the recombinant strain PGAe as template for lane 2;

(e) M is marker; lane 1 and 2 are fragments verified by PCR amplification using KAN-S/GB-X as primer, and genome of the original strain α as template for lane 1 and genome of the recombinant strain PGAe as template for lane 2;

(f) M is marker; lane 1 and 2 are fragments verified by PCR amplification using Kan-U/Kan-D as primer, and genome of the recombinant strain 1 before the knockout of KanMX as template for lane 1 and genome of the recombinant strain PGAe after the knockout of KanMX as template for lane 2.

(g) M is marker; lane 1 and 2 are fragments verified by PCR amplification using Zeocin-U/Zeocin-D as primer, and genome of recombinant strain 1 before passaging as template for lane 1 and genome of the recombinant strain PGAe after passaging as template for lane 2.

Figure 5:
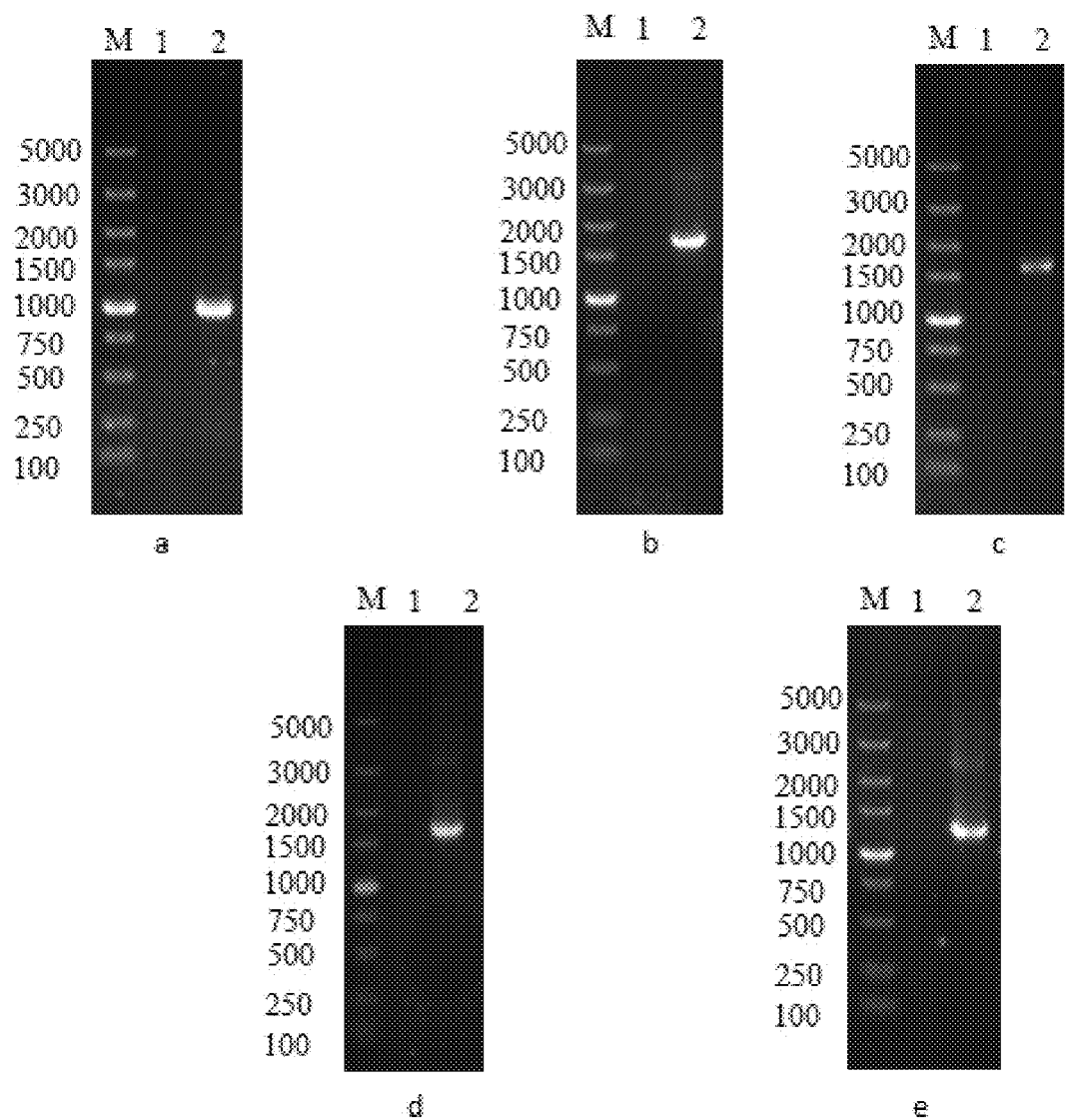

FIG. 5 shows the PCR verification of the recombinant of intracellular integrated alcohol dehydrogenase gene ADH2, wherein:

(a) M is marker; lane 1 and 2 are fragments verified by PCR amplification using IA-S/PGK1$_P$-X as primer, and genome of the original strain α as template for lane 1 and genome of the recombinant strain PGA2Ae as template for lane 2;

(b) M is marker; lane 1 and 2 are fragments verified by PCR amplification using PGK1$_P$-S/PGK1$_T$-X as primer, and genome of the original strain α as template for lane 1 and genome of the recombinant strain PGA2Ae as template for lane 2;

(c) M is marker; lane 1 and 2 are fragments verified by PCR amplification using KAN-S/IA-X as primer, and genome of the original strain α as template for lane 1 and genome of the recombinant strain PGA2Ae as template for lane 2;

(d) M is marker; lane 1 and 2 are fragments verified by PCR amplification using Kan-U/Kan-D as primer, and genome of the recombinant strain 2 before the knockout of KanMX as template for lane 1 and genome of the recombinant strain PGA2Ae after the knockout of KanMX as template for lane 2;

(e) M is marker; lane 1 and 2 are fragments verified by PCR amplification using Zeocin-U/Zeocin-D as primer, and genome of the recombinant strain 1 before passaging as template for lane 1 and genome of recombinant strain PGA2Ae after passaging as template for lane 2.

Figure 6:
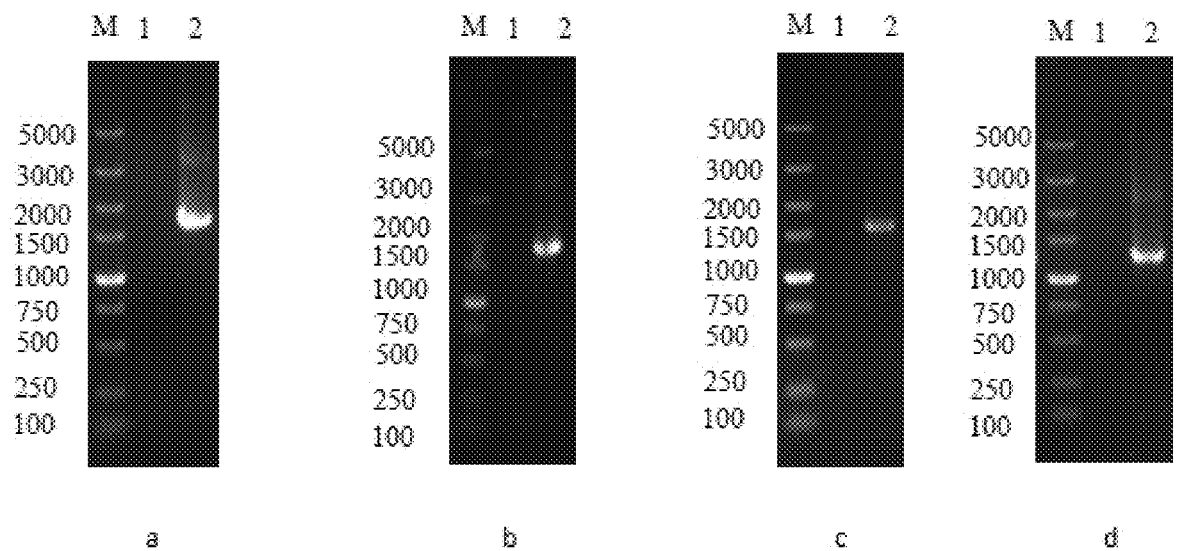

FIG. 6 shows the PCR verification of the recombinant after the intracellular knockout of the porin gene POR2, wherein:

(a) M is marker; lane 1 and 2 are fragments verified by PCR amplification using PA-S/KAN-X as primer, and genome of the original strain α as template for lane 1 and genome of the recombinant strain PGA2AeΔPor2 as template for lane 2;

(b) M is marker; lane 1 and 2 are fragments verified by PCR amplification using KAN-S/PB-X as primer, and genome of the original strain α as template for lane 1 and genome of the recombinant strain PGA2AeΔPor2 as template for lane 2;

(c) M is marker; lane 1 and 2 are fragments verified by PCR amplification using Kan-U/Kan-D as primer, and genome of the recombinant strain 3 before the knockout of KanMX as template for lane 1 and genome of the recombinant strain PGA2AeΔPor2 after the knockout of KanMX as template for lane 2;

(d) M is marker; lane 1 and 2 are fragments verified by PCR amplification using Zeocin-U/Zeocin-D as primer, and genome of the recombinant strain 1 before passaging as template for lane 1 and genome of the recombinant strain PGA2AeΔPor2 after passaging as template for lane 2.

Figure 7:
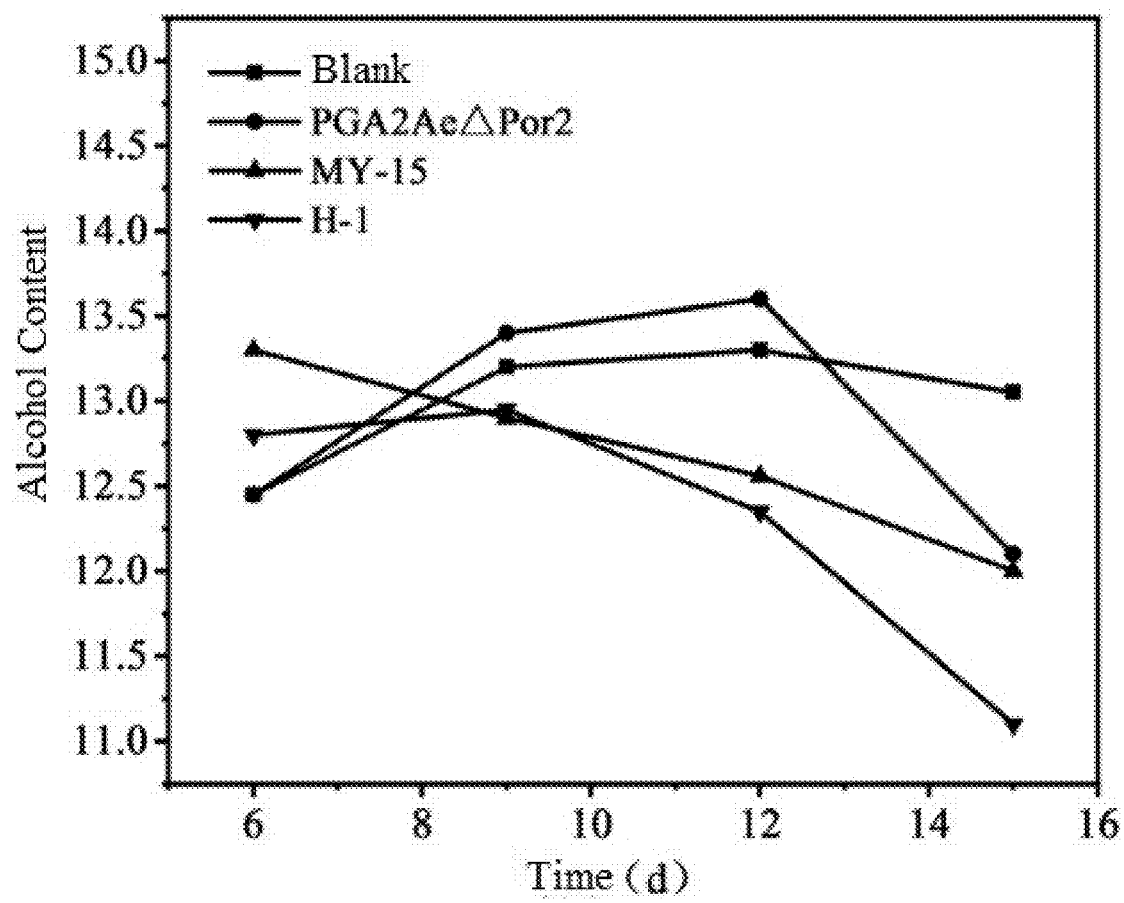

FIG. 7 shows the alcohol content of different fermentation systems determined in samples taken at specific time intervals during the experiment on Chi Xiang Xing Baijiu fermentation with yeast strains.

Figure 8:
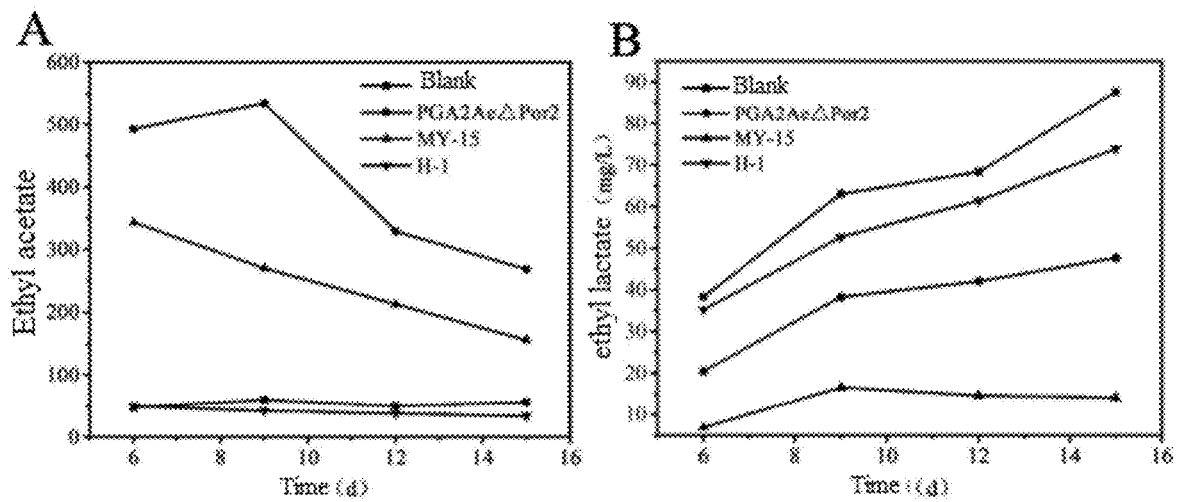

FIG. 8 shows the changes in levels of ethyl acetate (A) and ethyl lactate (B) with time in Zhaijiu fermentation systems with PGA2AeΔPor2, MY-15 and H-1 strains.

Figure 9:
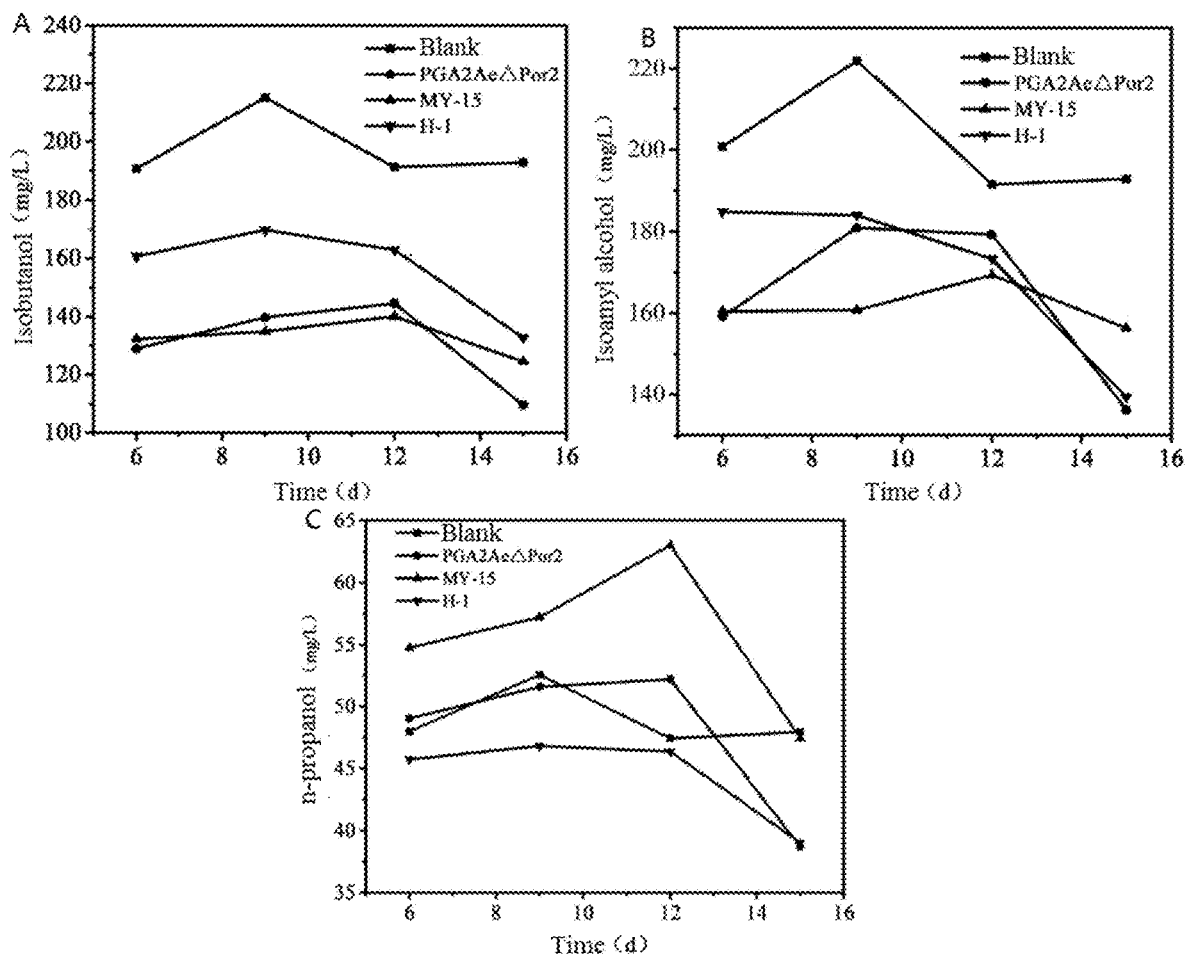

FIG. 9 shows the changes in levels of various higher alcohols (A: isobutanol; B: isoamyl alcohol; C: n-propanol) with time in Zhaijiu fermentation systems with PGA2AeΔPor2, MY-15 and H-1 strains.

Figure 10:
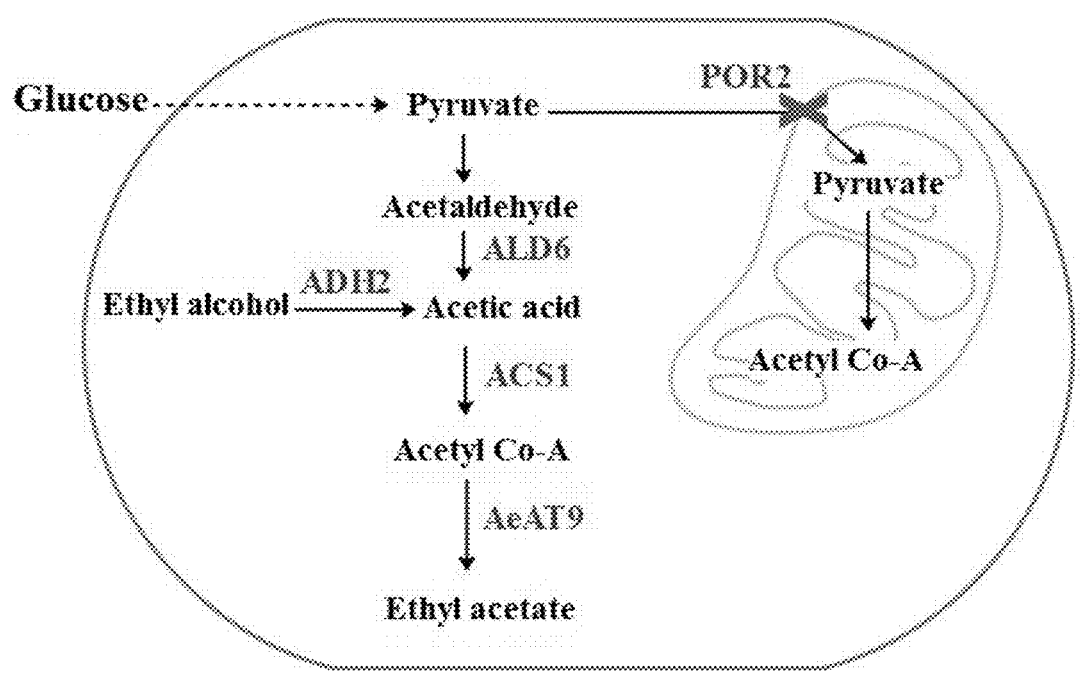

FIG. 10 shows the schematic diagram of a biosynthesis pathway of ethyl acetate in the genetically engineered strain of Saccharomyces cerevisiae constructed in the present disclosure.

DESCRIPTION OF THE EMBODIMENTS

The present disclosure is described below through specific embodiments. Unless otherwise specified, the technical means used in the present disclosure are all methods known to those skilled in the art. In addition, the embodiments should be understood as illustrative, rather than limiting the scope of the disclosure; the substance and the scope of the disclosure are only limited by the claims. For those skilled in the art, without departing from the substance and scope of the present disclosure, various changes or modifications to the material composition and amount used in these embodiments also belong to the protection scope of the present disclosure.

In the first aspect, a genetically engineered strain of Saccharomyces cerevisiae is provided in the present disclosure, the engineered strain heterogeneously overexpresses an acetaldehyde dehydrogenase gene ALD6, an acetyl-CoA synthase gene ACS1 and an alcohol acyltransferase gene AeAT9.

According to the present disclosure, in at least one embodiment, the acetaldehyde hydrogenase gene ALD6 has a nucleotide sequence as shown in SEQ ID NO:1 and a Gene ID 856044.

In some embodiments, the acetaldehyde hydrogenase gene ALD6 is connected to a strong promoter of gene PGK1 and a terminator of gene GIC1. In at least one embodiment of the present disclosure, the strong promoter is PGK1$_P$ with a Gene ID: 850370 and a preferable nucleotide sequence as shown in SEQ ID NO:7; the strong terminator is GIC1$_T$ with a Gene ID: 856458 and a preferable nucleotide sequence as shown in SEQ ID NO:8.

According to the present disclosure, in at least one embodiment, the acetyl-CoA synthase gene ACS1 has a nucleotide sequence as shown in SEQ ID NO:2 and a Gene ID: 851245.

In some embodiments, the acetyl-CoA synthase gene ACS1 is connected to a strong promoter of gene TEF1 and a terminator of gene PGK1. In at least one embodiment of the present disclosure, the strong promoter is TEF1$_P$ with a Gene ID: 856195 and a preferable nucleotide sequence as shown in SEQ ID NO:9; the terminator is PGK1$_T$ with a Gene ID: 850370 and a preferable nucleotide sequence as shown in SEQ ID NO:10.

According to the present disclosure, in at least one embodiment, the alcohol acyltransferase gene AeAT9 has a nucleotide sequence as shown in SEQ ID NO:4 and derives from kiwi fruit, and the Protein ID thereof is AIC83789.1.

In some embodiments, the alcohol acyltransferase gene AeAT9 is connected to a strong promoter of gene PGK1 and a terminator of gene PGK1. In at least one embodiment of the present disclosure, the strong promoter is PGK1$_P$ with a Gene ID: 850370 and a preferable nucleotide sequence as shown in SEQ ID NO:7; the terminator is PGK1$_T$ with a Gene ID: 850370 and a preferable nucleotide sequence as shown in SEQ ID NO:10.

In at least one embodiment of the present disclosure, the acetyl-coA synthetase gene ACS1, the aldehyde dehydrogenase gene ALD6 and the alcohol acyltransferase gene AeAT9 are sequentially connected in the genetically engineered strain of Saccharomyces cerevisiae.

According to the present disclosure, the acetyl-coA synthetase gene ACS1, the aldehyde dehydrogenase gene ALD6 and the alcohol acyltransferase gene AeAT9 can be inserted into any position in *Saccharomyces cerevisiae*, as long as the fermentation performance of *Saccharomyces cerevisiae* is not affected and expression can be achieved. In order to further improve the yield of ethyl acetate, in at least one embodiment, the acetyl-coA synthetase gene ACS1, the aldehyde dehydrogenase gene ALD6 and the alcohol acyltransferase gene AeAT9 are sequentially connected, and inserted into the coding gene Gal80 region of the transcription regulator of galactose in the *Saccharomyces cerevisiae*, and replace it. That is, the coding gene Gal80 of the galactose transcription regulator in the *Saccharomyces cerevisiae* is knocked out and original place thereof is replaced by the above-mentioned linked genes.

The coding gene Gal80 of the galactose transcription regulator has a nucleotide sequence as shown in SEQ ID NO: 6, and the Gene ID thereof is 854954.

According to the present disclosure, in order to further improve the yield of ethyl acetate, in at least one embodiment, the engineered strain further heterogeneously overexpresses an alcohol dehydrogenase gene ADH2.

In at least one embodiment, the alcohol dehydrogenase gene ADH2 has a nucleotide sequence as shown in SEQ ID NO:3, and the Gene ID thereof is 855349.

In at least one embodiment, the alcohol dehydrogenase gene ADH2 is connected to an inducible promoter of gene HTX7 and a terminator of gene PGK1. In one embodiment of the present disclosure, the inducible promoter is $HTX7_p$ with a preferable nucleotide sequence as shown in SEQ ID NO: 11; the terminator is $PGK1_T$ with a preferable nucleotide sequence as shown in SEQ ID NO: 10.

According to the present disclosure, the alcohol dehydrogenase gene ADH2 can be inserted into any position in *Saccharomyces cerevisiae*, as long as the fermentation performance of *Saccharomyces cerevisiae* is not affected and expression cassette can be expressed. In order to further improve the yield of ethyl acetate, in at least one embodiment, the alcohol dehydrogenase gene ADH2 is inserted at a site of, and replace an isoamyl acetate hydrogenase gene IAH1 (Gene ID854293) of *Saccharomyces cerevisiae*. That is, the isoamyl acetate hydrogenase gene IAH1 of *Saccharomyces cerevisiae* is knocked out and replaced by the alcohol dehydrogenase gene ADH2.

In at least one embodiment, the isoamyl acetate hydrogenase gene IAH1 has a nucleotide sequence as shown in SEQ ID NO: 12.

According to the present disclosure, in order to further improve the yield of ethyl acetate, the engineered strain does not express a porin gene POR2 responsible for transporting cytosolic pyruvate into the mitochondria.

In at least one embodiment, the porin gene POR2 responsible for transporting cytosolic pyruvate into the mitochondria has a nucleotide sequence as shown in SEQ ID No:5, and the Gene ID thereof is 854692.

According to the present disclosure, conventional means in the art can be used so that the porin gene POR2 is not expressed; for example, the gene can be inactivated or knocked out by conventional means in the art.

According to the present disclosure, "do not express" means that the expression level of the porin gene POR2 is significantly reduced by, for example, at least 50%, 60%, 70%, 80%, 90% and 100%, compared to the original expression level.

In at least one embodiment of the present disclosure, the porin gene POR2 of the genetically engineered strain responsible for transporting cytosolic pyruvate into the mitochondria is knocked out. The knockout method thereof can be conventional means in the art, for example, knockout by homologous recombination, preferably, knockout the porin gene POR2 through homologous recombination of the resistance gene KanMX and the porin gene POR2. It can be understood that after the knockout of the porin gene POR2 by said method, the genetically engineered strain of *Saccharomyces cerevisiae* will contain the resistance gene KanMX.

According to the present disclosure, the original strain for constructing the genetically engineered strain of *Saccharomyces cerevisiae* can be any *Saccharomyces cerevisiae* strain. In at least one embodiment of the present disclosure, the original strain is *Saccharomyces cerevisiae* CICC32315.

According to one embodiment of the present disclosure, the genetically engineered strain of *Saccharomyces cerevisiae* heterogeneously overexpresses genes related to the formation of cytosolic acetyl-CoA, i.e., alcohol dehydrogenase gene ADH2, acetaldehyde dehydrogenase gene ALD6 and acetyl-CoA synthase gene ACS1, fortifying the synthesis of cytosolic acetyl-CoA; meanwhile the alcohol acyltransferase gene AeAT9 from green plants is heterogeneously overexpressed to promote the synthesis of ethyl acetate; and further, on the basis of the overexpression of the above-mentioned genes, the porin gene POR2 responsible for transporting cytosolic pyruvate to the mitochondria is knocked out, thus partially blocking the transport of cytosolic pyruvate to the mitochondria so that the carbon metabolic flux flows as much as possible to the cytosolic acetyl CoA, further promoting the synthesis of cytosolic ethyl acetate.

In the second aspect, a method for constructing the above-mentioned genetically engineered strain of *Saccharomyces cerevisiae* is provided in the present disclosure, comprising: the aldehyde dehydrogenase gene ALD6, the acetyl-CoA synthase gene ACS1, the alcohol acyltransferase gene AeAT9 and optionally the alcohol dehydrogenase gene ADH2 are introduced into *Saccharomyces cerevisiae*; and optionally, the porin gene POR2 responsible for transporting cytosolic pyruvate into the mitochondria is inactivated or knocked out.

A detailed description has been made in the first aspect of the present disclosure regarding the selection of each gene, of promoters and terminators, and of original strains and so on. In order to avoid unnecessary repetition, those already covered in the first aspect will not be repeated here.

A specific embodiment according to the present disclosure, the constructing method comprises:

firstly, the acetaldehyde dehydrogenase gene ALD6, the acetyl-CoA synthase gene ACS1 and the alcohol acyltransferase gene AeAT9 were simultaneously overexpressed in a yeast strain to obtain a yeast strain PGAe with certain yield of ethyl acetate;

secondly, the alcohol dehydrogenase gene ADH2 was overexpressed to obtain a strain PGA2Ae with further increased yield of ethyl acetate;

and finally, the porin gene POR2 of the strain PGA2Ae was knocked out to obtain the ethyl acetate-producing yeast strain PGA2AeΔPor2;

further, the simultaneous overexpression of the acetaldehyde dehydrogenase gene ALD6, the acetyl-CoA synthase gene ACS1 and the alcohol acyltransferase gene AeAT9 was achieved by replacing the coding gene Gal80 of a transcription regulator in *Saccharomyces cerevisiae*. As described in the first aspect, in at least one embodiment, the acetyl-CoA synthase gene ACS1, the aldehyde dehydrogenase gene ALD6, and the alcohol acyltransferase gene AeAT9 were sequentially connected to form linked genes, which were then performed homologous recombination with the coding gene Gal80 of a transcription regulator to knock Gal80 out, and inserted into the position of the coding gene Gal80 of the transcription regulator.

Further, the overexpression of the alcohol dehydrogenase gene ADH2 was achieved by replacing the isoamyl acetate hydrogenase gene IAH1 of *Saccharomyces cerevisiae*. As described in the first aspect, in at least one embodiment, the isoamyl acetate hydrogenase gene IAH1 was knocked out by homologous recombination thereof with the alcohol dehydrogenase gene ADH2, and the linked genes were inserted into the position of the isoamyl acetate hydrogenase gene IAH1.

Further, the porin gene POR2 was knocked out by homologous recombination thereof with a resistance gene KanMX.

In a further embodiment according to the present disclosure, the method for constructing the genetically engineered strain of *Saccharomyces cerevisiae* with high yield of ethyl acetate comprises the following steps:

(1) constructing an ethyl acetate-producing *Saccharomyces cerevisiae* strain which simultaneously overexpresses genes ACS1, ALD6 and AeAT9.

1) PCR method was employed using the genome of the original yeast strain as template and the transcription regulator gene Gal80 as integration site to obtain fragments containing homologous sequences of the upstream and downstream genes, including the promoter and upstream homology arm fragment GA of the gene Gal80, the downstream homology arm fragment GB of gene Gal80, the promoter $TEF1_P$, the acetyl-CoA synthase gene ACS1 and the terminator $PGK1_T$;

2) the fragments GA and $TEF1_P$, fragments ACS1 and $PGK1_T$ were fused separately by the fusion PCR method to obtain two fusion fragments GA-$TEF1_P$ and ACS1-$PGK1_T$;

3) the fusion fragments GA-$TEF1_P$ and ACS1-$PGK1_T$ were further fused by the fusion PCR method to obtain the fusion fragment GA-$TEF1_P$-ACS1-$PGK1_T$;

4) PCR amplification was carried out using genome of the original yeast strain as template to obtain the following fragments separately: the aldehyde dehydrogenase gene ALD6, the promoter $PGK1_p$ and terminator GIC1 containing the homologous sequence of gene ALD6.

5) the three fragments ALD6, $PGK1_p$ and $GIC1_T$ were fused by the fusion PCR method to obtain the fusion fragment $PGK1_P$-ALD6-GIC1 T;

6) PCR amplification of AeAT9 was carried out using pUC57-AeAT9 plasmid as template; 7) PCR amplification was carried out using genome of the original yeast strain as template to obtain the promoter $PGK1_P$ and terminator $PGK1_T$ containing the homologous sequence of gene AeAT9;

8) the fragments $PGK1_P$, $PGK1_T$ and AeAT9 were fused by the fusion PCR method to obtain the fusion fragment $PGK1_P$-AeAT9-$PGK1_T$;

9) PCR amplification was carried out using pUG6 plasmid as template to obtain the gene KanMX;

10) the fragments KanMX and GB were further fused by the fusion PCR method to obtain the fusion fragment KanMX-GB;

11) the above-mentioned fragments with homology regions of adjacent fragments obtained by PCR, i.e., GA-$TEF1_P$-ACS1-$PGK1_T$, $PGK1_P$-ALD6-$GIC1_T$, $PGK1_P$-AeAT9-$PGK1_T$ and KanMX-GB, were introduced into the original *Saccharomyces cerevisiae* strain through lithium acetate transformation to obtain a recombinant strain.

12) the KanMX gene in the recombinant strain of step 11) was removed by pGAPza plasmid to obtain a recombinant strain without the KanMX gene, and a recombinant strain PGAe without the pGAPza plasmid was obtained after passaging.

(2) Constructing an ethyl acetate-producing *Saccharomyces cerevisiae* strain which overexpresses gene ADH2.

1) PCR method was employed using genome of the original yeast strain as template and gene IAH1 as integration site to obtain an upstream homology arm fragment IA and a downstream homology arm fragment IB of gene IAH1;

2) PCR amplification was carried out using genome of the original yeast strain as template to obtain the following fragments: the aldehyde dehydrogenase gene ADH2, the promoter $PGK1_p$ and the terminator $PGK1_T$ containing the homologous sequence of gene ADH2;

3) PCR amplification was carried out using pUG6 plasmid as template to obtain gen KanMX containing the homology region of IB;

4) the fragments IA, $PGK1_P$ and ADH2 were fused once by the fusion PCR method to obtain a fusion fragment IA-$PGK1_P$-ADH2;

5) the fragments $PGK1_T$, KanMX and IB were fused by the fusion PCR method to obtain a fusion fragment $PGK1_T$-KanMX-IB;

6) the above-mentioned fragments containing the homology regions of adjacent fragments obtained by PCR, i.e., IA-$PGK1_P$-ADH2 and $PGK1_T$-KanMX-IB, were introduced into the recombinant strain PGAe of step (1)-12) through lithium acetate transformation to obtain a recombinant strain of *Saccharomyces cerevisiae* with further high yield of ethyl acetate after homologous recombination.

7) gene KanMX of the recombinant strain of step 6) was removed using pGAPza plasmid to obtain a recombinant strain without gene KanMX, and a recombinant strain PGA2Ae without the pGAPza plasmid was obtained after passaging.

(3) Constructing an ethyl acetate-producing *Saccharomyces cerevisiae* strain where the porin gene POR2 was knocked out.

1) PCR method was employed using genome of the original yeast strain as template to obtain the following fragments containing gene KanMX: an upstream homology arm fragment PA of gene POR2 and a downstream homology arm fragment PB of gene POR2;

2) PCR amplification was carried out using pUG6 plasmid as template to obtain gene KanMX containing the homologous sequence of the upstream and downstream homology arm fragments of gene POR2;

3) the above-mentioned fragments with homology regions of adjacent fragments obtained by PCR, i.e., PA, KanMx and PB, were each introduced into the recombinant strain PGA2Ae of step (2)-7) through lithium acetate transformation to obtain a recombinant strain of *Saccharomyces cerevisiae* with further high yield of ethyl acetate after homologous recombination.

4) gene KanMX of the strain of step 3) was removed by pGAPza plasmid to obtain a recombinant strain without gene KanMX, and a recombinant strain PGA2AeΔPor2 without the pGAPza plasmid was obtained after passaging.

The procedures involved in the above-mentioned constructing processes have been reported abundantly in literature, such as Molecular Cloning: A Laboratory Manual (Second Edition, Science Press, 1995) by Joseph Sambrook et al.

In the third aspect, use of the genetically engineered strain of Saccharomyces cerevisiae in brewing is provided in the present disclosure.

The strain presents a strong capacity of ethyl acetate synthesis during the high-acidity Baijiu fermentation, and can significantly reduce the yield of higher alcohols, thus providing for broad application prospects for the fermentation and production of light-flavor Baijiu and even alcoholic beverages.

Moreover, the strain produces small amounts of isoamyl acetate and no isobutyl acetate during the ethanol fermentation.

Hereinafter, the present disclosure will be described in details through embodiments. In the following embodiments, unless otherwise specified, refer to Molecular Cloning: A Laboratory Manual (Second Edition, Science Press, 1995) by Joseph Sambrook et al. for the procedures involved in the embodiments of the present disclosure.

Embodiment 1: Construction of a New Saccharomyces cerevisiae Strain PGA2AeΔPor with High Yield of Ethyl Acetate The original strain used in this example was AY14 (Saccharomyces cerevisiae CICC32315). The YPD medium was a universal complete medium; the solid medium contained 2% agar powder.

The main procedure for constructing the strain is as follows:

(1) constructing an ethyl acetate-producing Saccharomyces cerevisiae strain which simultaneously overexpresses genes ACS1, ALD6 and AeAT9.

PCR amplification was carried out using genome of the yeast strain AY14-α as template and Gal80 as integration site; a 549-bp upstream homology arm fragment GA with the homology region of the promoter $TEF1_P$ was obtained when using the primer pair GA-U (SEQ ID NO: 13) and GA-D (SEQ ID NO: 14); a 502-bp downstream homology arm fragment GB with the homology region of the selectable marker Kan was obtained when using the primer pair GB-U (SEQ ID NO: 15) and GB-D (SEQ ID NO: 16); a 1001-bp promoter TEF1p fragment with the homology regions of GA and ACS1 was obtained when using the primer pair TEF1P-U (SEQ ID NO: 17) and TEF1P-D (SEQ ID NO: 18); a 258-bp terminator $PGK1_T$ fragment with the homology regions of ACS1 and $PGK1_P$ was obtained when using the primer pair $PGK1_T$-U (SEQ ID NO: 21) and $PGK1_T$-D (SEQ ID NO: 22); and a 2142-bp acetyl-CoA synthetase gene ACS1 with the homology regions of $TEF1_P$ and $PGK1_T$ was obtained when using the primer pair ACS1-U (SEQ ID NO: 19) and ACS1-D (SEQ ID NO: 20);

Similarly, PCR amplification was carried out using genome of AY14-α as the template, and a 1479-bp $PGK1_P$ fragment with the homology regions of $PGK1_P$ and ALD6 was obtained when using the primer pair $PGK1_P$-U (SEQ ID NO: 23) and $PGK1_P$-D (SEQ ID NO: 24); a 1503-bp ALD6 fragment with the homology regions of $PGK1_P$ and $GIC1_T$ was obtained when using the primer pair ALD6-U (SEQ ID NO: 25) and ALD6-D (SEQ ID NO: 26); and a 599-bp $GIC1_T$ fragment with the homology regions of ALD6 and $PGK1_P$ was obtained when using the primer pair GIC1T-U (SEQ ID NO: 27) and GIC1T-D (SEQ ID NO: 28);

PCR amplification was carried out, and a 1299-bp AeAT9 fragment containing the homology regions of $PGK1_P$ and $PGK1_T$ was obtained when using the pUC57-AeAT9 plasmid as template and using the primer pair AeAT9-U (SEQ ID NO: 31) and AeAT9-D (SEQ ID NO: 32); a 1479-bp $PGK1_P$ fragment with the homology region of AeAT9 was obtained when using genome of AY14-α as template and using the primer pair $PGK1_P$(G)-U (SEQ ID NO: 29) and $PGK1_P$(Ae)-D (SEQ ID NO: 30); and a 258-bp terminator $PGK1_T$ fragment with the homology regions of AeAT9 and Kan was obtained when using the primer pair PGK1T (Ae)-U (SEQ ID NO: 33) and PGK1T(Kan)-D (SEQ ID NO: 34).

PCR amplification was carried out using pUG6 plasmid as template, and a 1613-bp Kan fragment containing the homology regions of $PGK1_T$ and GB was obtained when using the primer pair Kan-U (SEQ ID NO: 35) and Kan (G)-D (SEQ ID NO: 36).

Figure 1:
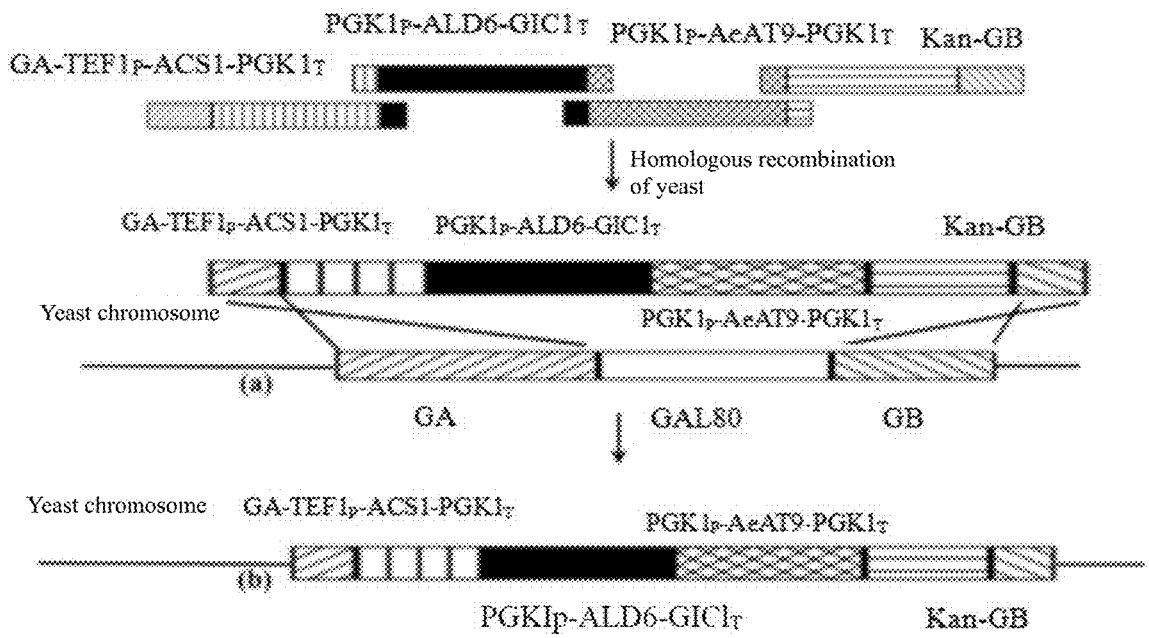
FIG. 1 shows the homologous recombination process for intracellular integration of the acetaldehyde dehydrogenase gene ALD6, the acetyl-CoA synthase gene ACS1, and the alcohol acyltransferase gene AeAT9.

The fragments GA and $TEF1_P$, fragments ACS1 and $PGK1_T$ were fused respectively using the fusion PCR method to obtain a GA-$TEF1_P$ fragment and an ACS1-$PGK1_T$ fragment, which were further fused to obtain a 3949-bp fragment GA-$TEF1_P$-ACS1-$PGK1_T$. Similarly, fragments $PGK1_P$, ALD6 and $GIC1_T$ were fused by the fusion PCR method to obtain a 3581-bp fragment $PGK1_P$-ALD6-$GIC1_T$; and fragments $PGK1_P$, AeAT9 and $PGK1_T$ were fused by the fusion PCR method to obtain a 3036-bp fragment $PGK1_P$-AeAT9-$PGK1_T$. Fragments Kan and GB were fused by the fusion PCR method to obtain a 2115-bp fragment Kan-GB. The fragments GA-$TEF1_P$-ACS1-$PGK1_T$, $PGK1_P$-ALD6-$GIC1_T$, $PGK1_P$-AeAT9-$PGK1_T$ and KanMX-GB were introduced into the original strain of Saccharomyces cerevisiae through lithium acetate transformation to obtain a recombinant strain of Saccharomyces cerevisiae PGAe-Kan with yield of ethyl acetate after homologous recombination. The homologous recombination process is shown as in FIG. 1.

Verification of the recombinant strain of Saccharomyces cerevisiae:

Five sets of verification primers were designed according to the gene sequences at both ends of the recombination site and according to the inserted homologous recombination sequence in Saccharomyces cerevisiae. The recombinant was verified by PCR amplification using genome of the better-growing transformant as template.

The cultured bacteria liquid obtained by the lithium acetate transformation and repair was washed with water and then coated on a YEPD screening plate containing 300 mg/L of G418 resistance. After 2 days' culture at 30° C., a larger single colony was picked for verification. The faster-growing transformant was used as template, and genome of the original strain AY14-α was used as a negative control, five primer pairs were selected for verification. The first primer pair GA-S/TEF1-X (SEQ ID NO: 55/56) was used to verify whether the homologous recombination of the homology arm GA and the homologous sequence on the left side of gene Gal80 in the chromosomes occur. The upstream cross-PCR verification method was used in the present disclosure, and bands were obtained under 0.8%-1% agarose gel electrophoresis as shown in (a) in FIG. 4, both of which were 1620 bp in size, while the original strain cannot be amplified as a negative control. The second primer pair ACS1-S (SEQ ID NO: 57) and $PGK1_p$-X (SEQ ID NO: 58) was used to verify whether the homologous recombination occur between the terminator on gene ACS1 and the promoter $PGK1_p$ of ALD6. The upstream cross-PCR verification method was used in the present disclosure, and two bands were obtained under 0.8%-1% agarose gel electrophoresis as shown in (b) in FIG. 4, both of which were 2781 bp in size, while the original strain cannot be amplified as a negative control. The third primer pair ALD6-S/PGK1$_p$-X (SEQ ID NO: 59/58) was used to verify whether the homologous recombination occur between the terminator on gene ALD6 and the promoter PGK1$_p$ of gene AeAT9. The upstream cross-PCR verification method was used in the present disclosure, and two bands were obtained under 0.8%-1% agarose gel electrophoresis as shown in (c) in FIG. 4, both of which were 1400 bp in size, while the original strain cannot be amplified as a negative control. The fourth primer pair PGK1$_T$-U/KAN-X (SEQ ID NO: 60/61) was used to verify whether the homologous recombination occur between the terminator on gene AeAT9 and KAN. The upstream cross-PCR verification method was used in the present disclosure, and two bands were obtained under 0.8%-1% agarose gel electrophoresis as shown in (d) in FIG. 4, both of which were 1200 bp in size, while the original strain cannot be amplified as a negative control. The fifth primer pair KAN-S/GB-X (SEQ ID NO: 62/63) was used to verify whether the homologous recombination occur between the homology arm B and the homologous sequence on the right side of gene Gal80 in the chromosomes. The downstream cross-PCR verification method was used in the present disclosure, and bands were obtained under 0.8%-1% agarose gel electrophoresis as shown in (e) in FIG. 4, which was 1817 bp in size, while the original strain cannot be amplified as a negative control. It was demonstrated that the recombination cassette GA-TEF1P-ACS1-PGK1T-PGK1$_p$-ALD6-GIC1T-PGK1$_p$-AeAT9-PGK1T-KanMX-GB was successfully recombined into the genome of Saccharomyces cerevisiae AY14-α at a correct recombination position. The electrophoresis result is shown in FIG. 4 as the verification result of the recombinant strain of Saccharomyces cerevisiae.

Figure 4:
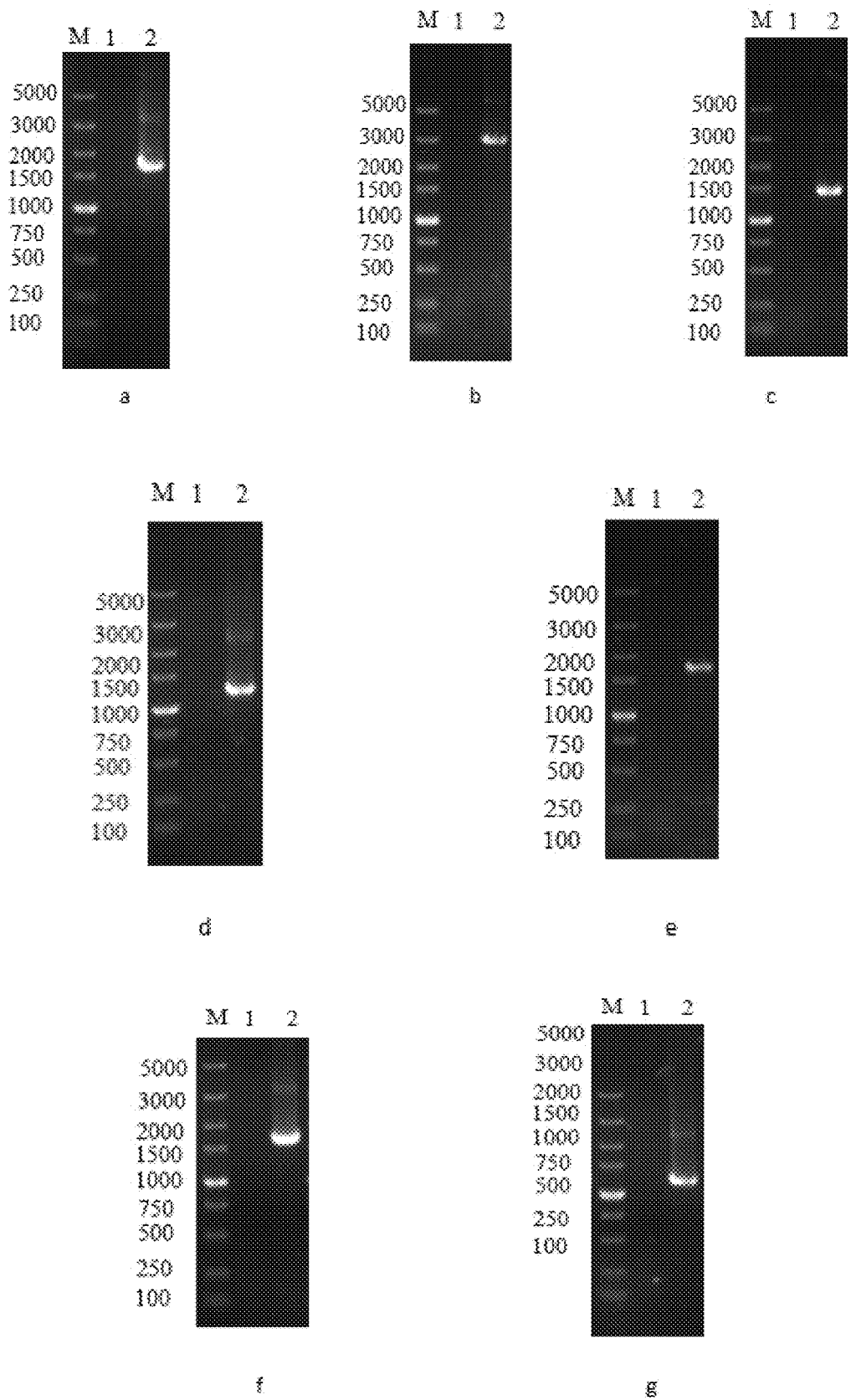
FIG. 4 shows the PCR verification of the recombinant of intracellular integrated acetaldehyde dehydrogenase gene ALD6, the acetyl-CoA synthase gene ACS1, and the alcohol acyltransferase gene AeAT9, wherein: (a) M is marker; lane 1 and 2 are fragments verified by PCR amplification using GA-S/TEF1-X as primer, and genome of the original strain α as template for lane 1 and genome of the recombinant strain PGAe as template for lane 2.

In (a) in FIG. 4, M is a 5000-bp DNA Ladder Marker; lane 1 and 2 are fragments verified by PCR amplification using GA-S/TEF1-X as primer, and genome of the original strain α as template for lane 1, and genome of the recombinant strain PGAe as template for lane 2;

In (b) in FIG. 4, M is a 5000-bp DNA Ladder Marker; lane 1 and 2 are fragments verified by PCR amplification using ACS1-S/PGK1$_p$-X as primer, and genome of the original strain α as template for lane 1, and genome of the recombinant strain PGAe as template for lane 2;

In (c) in FIG. 4, M is a 5000-bp DNA Ladder Marker; lane 1 and 2 are fragments verified by PCR amplification using ALD6-S/PGK1$_p$-X as primer, and genome of the original strain α as template for lane 1, and genome of the recombinant strain PGAe as template for lane 2;

In (d) in FIG. 4, M is a 5000-bp DNA Ladder Marker; lane 1 and 2 are fragments verified by PCR amplification using PGK1t-U/KAN-X as primer, and genome of the original strain α as template for lane 1, and genome of the recombinant strain PGAe as template for lane 2;

In (e) in FIG. 4, M is a 5000-bp DNA Ladder Marker; lane 1 and 2 are fragments verified by PCR amplification using KAN-S/FB-X as primer, and genome of the original strain α as template for lane 1, and genome of the recombinant strain PGAe as template for lane 2;

The pGAPza plasmid with Cre recombinase was transformed into recombinant strain PGAe-Kan by lithium acetate transformation to obtain the transformant PGAe-Kan-Cre; a single clone was picked and induced in galactose medium for 4-5 h before being diluted, and a single colony was picked and coated on a YEPD plate before being replica plated to a G418 resistance plate; strains that grew on the YEPD plate but not on the G418 resistance plate were picked out to extract the genome thereof for PCR verification, and no band of about 1600 bp was obtained when the above-mentioned genome was used as template to amplify the KanMX fragment, while the recombinant strain PGAe-Kan can be amplified to obtain the fragment. Results of the PCR verification is shown in (f) in FIG. 4. The verified single yeast colony was sub-cultured in YEPD liquid medium, and transferred every 12 h. The pGAPza plasmid was lost after several passages and a recombinant strain PGAe without the pGAPza plasmid was obtained. The yeast plasmid was extracted for PCR verification using Zeocin-F/Zeocin-R (SEQ ID NO: 53/54) as primer, as shown in (g) in FIG. 4.

(2) constructing an ethyl acetate-producing Saccharomyces cerevisiae strain which overexpresses gene ADH2.

Figure 2:
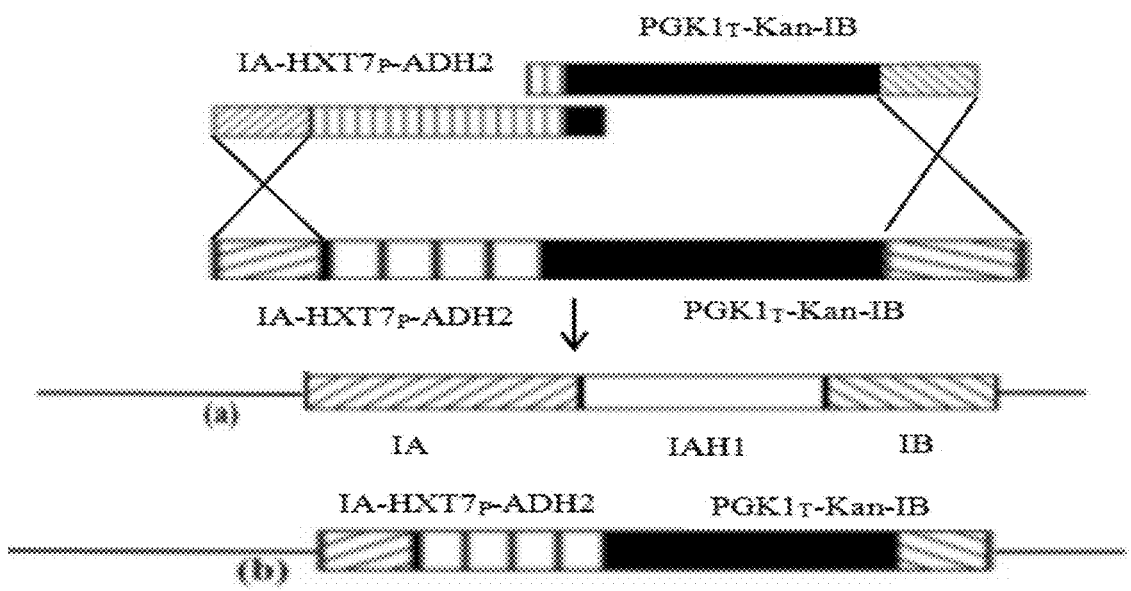
FIG. 2 shows the homologous recombination process for intracellular integration of the alcohol dehydrogenase gene ADH2.

PCR amplification was carried out using genome of the yeast strain AY14-α as template and IAH1 as integration site; a 478-bp upstream homology arm fragment IA with the homology region of the promoter PGK1$_P$ was obtained when using the primer pair IA-U (SEQ ID NO: 37) and IA-D (SEQ ID NO: 38); a 550-bp downstream homology arm fragment IB with the selection marker Kan homology region was obtained when using the primer pair IB-U (SEQ ID NO: 39) and IB-D (SEQ ID NO: 40); a 418-bp fragment of promoter PGK1$_P$ with the homology regions of IA and ADH2 was obtained when using the primer pair PGK1$_P$-U (SEQ ID NO: 41) and PGK1$_P$-D (SEQ ID NO: 42); a 258-bp fragment of terminator PGK1$_T$ with the homology regions of ADH2 and Kan was obtained when using the primer pair PGK1$_T$ (A)-U (SEQ ID NO: 45) and PGK1$_T$ (Kan)-D (SEQ ID NO: 34); a 1047-bp alcohol dehydrogenase gene ADH2 with the homology regions of PGK1$_p$ and PGK1$_T$ was obtained when using the primer pair ADH2-U (SEQ ID NO: 43) and ADH2-D (SEQ ID NO: 44); a 1613-bp Kan fragment was obtained when using the primer pair Kan-U (SEQ ID NO: 35) and Kan(I)-D (SEQ ID NO: 46);

Fragments IA, PGK1$_P$ and ADH2 were fused by the fusion PCR method to obtain a 1943-bp fragment IA-PGK1$_P$-ADH2, and PGK1$_T$ and Kan-IB were fused to obtain a 2421-bp fragment PGK1$_T$-Kan-IB. The fragments IA-PGK1$_P$-ADH2 and PGK1$_T$-Kan-IB were each introduced into the original strain PGAe of Saccharomyces cerevisiae through lithium acetate transformation to obtain an ethyl acetate-producing recombinant strain of Saccharomyces cerevisiae PGA2Ae-Kan after homologous recombination. The homologous recombination process is shown as in FIG. 2.

Verification of the Recombinant Strain of Saccharomyces cerevisiae:

Three sets of up-, middle-, and downstream primers were designed according to the gene sequences at both ends of the recombination site and according to the inserted homologous recombination sequence in Saccharomyces cerevisiae. The recombinant was verified by PCR amplification using the genome of the better-growing transformant as template.

The single colony obtained by the lithium acetate transformation was verified by up-, mid- and downstream fixed-point PCR amplification. The first primer pair IA-S/PGK1$_P$-X (SEQ ID NO: 64/65) was used to verify whether the homologous recombination of the homology arm IA and the homologous sequence on the left side of the gene IAH1 in the chromosomes occur. The upstream cross-PCR verification method was used in the present disclosure, and one band of about 958 bp was obtained under 0.8%-1% agarose gel electrophoresis as shown in (a) in FIG. 5, while the original strain cannot be amplified as a negative control. The second primer pair PGK1$_P$-S (SEQ ID NO: 66) and PGK1$_T$-X (SEQ ID NO: 67) was used to verify whether the homologous recombination of gene ADH2 and the terminator PGK1$_T$ occur. The upstream cross-PCR verification method was used in the present disclosure, and one band of about 1723 bp was obtained under 0.8%-1% agarose gel electrophoresis as shown in (b) in FIG. 5, while the original strain cannot be amplified as a negative control. The third primer pair Kan-S/IA-X (SEQ ID NO: 68/69) was used to verify whether the homologous recombination of the homology arm B and the homologous sequence on the right side of the gene IAH1 in the chromosomes occur. The downstream cross-PCR verification method was used in the present disclosure, and one band of about 2303 bp was obtained under 0.8%-1% agarose gel electrophoresis as shown in (c) in FIG. 5, while the original strain cannot be amplified as a negative control. It was demonstrated that the recombination cassette IA-PGK1$_P$-ADH2-PGK1T-KanMX-IB was successfully recombined into the genome of *Saccharomyces cerevisiae* AY14-α at a correct recombination position. The electrophoresis result is shown in FIG. 5 as the verification result of the recombinant strain of *Saccharomyces cerevisiae*.

In (a) in FIG. 5, M is a 5000-bp DNA Ladder Marker; lane 1 and 2 are fragments verified by PCR amplification using IA-S/PGK1$_P$-X as primer, and genome of the original strain α as template for lane 1 and genome of the recombinant strain PGA2Ae as template for lane 2;

In (b) in FIG. 5, M is a 5000-bp DNA Ladder Marker; lane 1 and 2 are fragments verified by PCR amplification using PGK1$_P$-S/PGK1$_T$-X as primer, and genome of the original strain α as template for lane 1 and genome of the recombinant strain PGA2Ae as template for lane 2;

In (c) in FIG. 5, M is a 5000-bp DNA Ladder Marker; lane 1 and 2 are fragments verified by PCR amplification using Kan-S/IA-X as primer, and genome of the original strain α as template for lane 1 and genome of the recombinant strain PGA2Ae as template for lane 2;

The pGAPza plasmid with Cre recombinase was transformed into recombinant strain by lithium acetate transformation to obtain the transformant PGA2Ae-Kan-Cre; a single clone was picked and induced in galactose medium for 4-5 h before being diluted, and a single colony was picked and coated on a YEPD plate before being replica plated to a G418 resistance plate; strains that grew on the YEPD plate but not on the G418 resistance plate were picked out to extract the genome thereof for PCR verification, and no band of about 1600 bp was obtained when the above-mentioned genome was used as template to amplify the KanMX fragment, while the recombinant strain PGA2Ae-Kan can be amplified to obtain the fragment. Results of the PCR verification is shown in (d) in FIG. 5. The verified single yeast colony was sub-cultured in YEPD liquid medium, and transferred every 12 h. The pGAPza plasmid was lost after several passages and a recombinant strain PGA2Ae without the pGAPza plasmid was obtained. The yeast plasmid was extracted for PCR verification using Zeocin-F/Zeocin-R (SEQ ID NO: 53/54) as the primer as shown in (e) in FIG. 5.

(3) constructing an ethyl acetate-producing *Saccharomyces cerevisiae* strain where the porin gene POR2 was knocked out.

Figure 3:
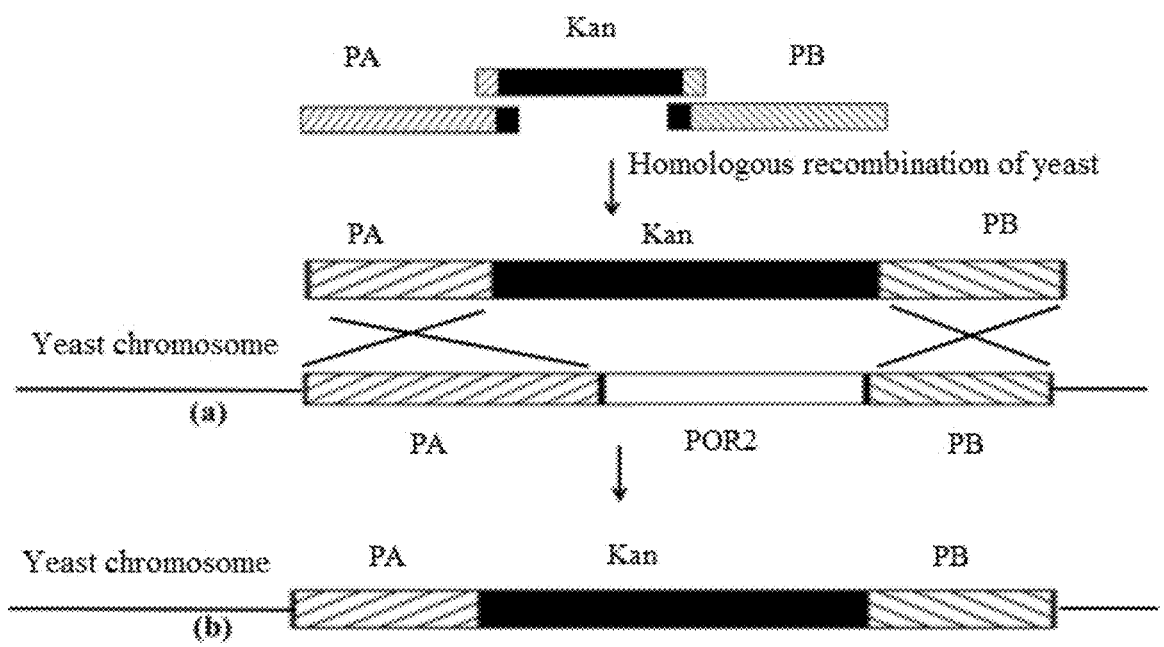
FIG. 3 shows the homologous recombination process for intracellular knockout of the porin gene POR2.

Similarly, PCR amplification was carried out using genome of the strain AY14-α as template; a 500-bp fragment PA with the homology region of Kan was obtained when using the primer pair PA-U (SEQ ID NO: 47) and PA-D (SEQ ID NO: 48); a 1613-bp fragment PB with the homology regions of PA and PB was obtained when using the primer pair Kan(P)-U (SEQ ID NO: 51) and Kan(P)-D (SEQ ID NO: 52); a 572-bp fragment PB with the homology region of Kan was obtained when using the primer pair PB-U (SEQ ID NO: 49) and PB-D (SEQ ID NO: 50); fragments PA, PB and Kan were each introduced into the original yeast strain through lithium acetate transformation to obtain an ethyl acetate-producing recombinant strain of *Saccharomyces cerevisiae* PGA2AeΔPor after homologous recombination. The homologous recombination is shown as in FIG. 3. The schematic diagram of the biosynthesis pathway of ethyl acetate by the recombinant strain PGA2AeΔPor of *Saccharomyces cerevisiae* is shown in FIG. 10.

Verification of the recombinant strain of *Saccharomyces cerevisiae*:

Two sets of upstream and downstream primers were designed according to the gene sequences at both ends of the recombination site and according to the inserted homologous recombination sequence in *Saccharomyces cerevisiae*. The recombinant was verified by PCR amplification using the genome of the better-growing transformant as template.

The single colony obtained by the lithium acetate transformation was verified by upstream and downstream fixed-point PCR amplification. The first primer pair PA-S-S/KAN-X (SEQ ID NO: 70/71) was used to verify whether the homologous recombination of the homology arm PA and the homologous sequence on the left side of the gene POR2 in the chromosomes occur. The upstream cross-PCR verification method was used in the present disclosure, and one band of about 1527 bp was obtained under 0.8%-1% agarose gel electrophoresis as shown in (a) in FIG. 6, while the original strain cannot be amplified as a negative control. The second primer pair KAN-S (SEQ ID NO: 72) and PB-X (SEQ ID NO: 73) was used to verify whether the homologous recombination of the homology arm B and the homologous sequence on the right side of the gene POR2 in the chromosomes occur. The upstream cross-PCR verification method was used in the present disclosure, and one band of about 1627 bp was obtained under 0.8%-1% agarose gel electrophoresis as shown in (b) in FIG. 6, while the original strain cannot be amplified as a negative control. It was demonstrated that the recombination cassette PA-KanMX-PB was successfully recombined into the genome of *Saccharomyces cerevisiae* AY14-α at a correct recombination position. The electrophoresis result is shown in FIG. 6 as the verification result of the recombinant strain of *Saccharomyces cerevisiae*.

In (a) in FIG. 6, M is a 5000-bp DNA Ladder Marker; lane 1 and 2 are fragments verified by PCR amplification using PA-S-S/KAN-X as primer, and genome of the original strain α as template for lane 1 and genome of the recombinant strain PGA2AeΔPor as template for lane 2;

In (b) in FIG. 6, M is a 5000-bp DNA Ladder Marker; lane 1 and 2 are fragments verified by PCR amplification using KAN-S/PB-X as primer, and genome of the original strain α as template for lane 1 and genome of the recombinant strain PGA2AeΔPor as template for lane 2;

The pGAPza plasmid with Cre recombinase was transformed into recombinant strain by lithium acetate transformation to obtain the transformant PGA2AeΔPor-Kan-Cre; a single clone was picked and induced in galactose medium for 4-5 h before being diluted, and a single colony was picked and coated on a YEPD plate before being replica plated to a G418 resistance plate; strains that grew on the YEPD plate but not on the G418 resistance plate were picked out to extract the genome thereof for PCR verification, and no band of about 1600 bp was obtained when the above-mentioned genome was used as template to amplify the KanMX fragment, while the recombinant strain can amplify to obtain the fragment. Results of the PCR verification is shown in (c) in FIG. 6. The verified single yeast colony was sub-cultured in YEPD liquid medium, and transferred every 12 h. The pGAPza plasmid was lost after several passages and a recombinant strain PGA2AeΔPor without the pGAPza plasmid was obtained. The yeast plasmid was extracted for PCR verification using Zeocin-F/Zeocin-R (SEQ ID NO: 53/54) as the primer as shown in (d) in FIG. 6.

Embodiment 2: Experiment of Corn Hydrolysate Fermentation with Strain PGA2AeΔPor2

Experiment of Corn-Based Liquid Baijiu Fermentation
1) Fermentation process flowchart: corn flour→soaking→liquefaction→saccharification→cooling→filtration→inoculation→fermentation→steaming→determination of indicators;
2) Process conditions:
soaking condition: 60-70° C., immersion for 20 min; liquefaction condition: 85-90° C., liquefaction for 90 min with thermostable α-amylase; saccharification condition: 55-60° C., saccharification for 20 h with glucoamylase;
3) Ingredients: corn flour 1500 g, water 4500 mL, standing for 20 min, thermostable α-amylase $2\times10^4$ U/mL, 0.9 ml, glucoamylase $1\times10^5$ U/mL, 3 mL.
4) Medium preparation:
Primary seed medium: 0.5% yeast extract powder was added to corn hydrolysate of 8° Brix, 5 ml thereof was aliquoted into a test tube, and boiled for 10 min for sterilization.
Secondary seed medium: 0.5% yeast extract powder was added to corn hydrolysate of 12° Brix, 45 mL thereof was aliquoted into a 150 mL Erlenmeyer flask, and sterilized for 15 min at 105° C.
Fermentation medium: corn hydrolysate of 18° Brix was prepared, and 135 mL thereof was aliquoted into a 250 mL triangular flasks, and sterilized at 105° C. for 15 min, after cooling to room temperature, 1 mL of nutrient salt ($MgSO_4$ 150 g/L, $KH_2PO_4$ 75 g/L, urea 81 g/L, filtered and stored at 4° C.) was added.

A full loop of Saccharomyces cerevisiae was picked and transferred to a tube containing 5 mL of primary seed medium for static culture at 30° C. for 24 h; then inoculated to a 150 mL triangular flask containing 45 mL secondary seed medium with a 10% inoculum for static culture at 30° C. for 16 h to the late logarithmic stage, then inoculated into the fermentation medium of corn hydrolysate with a 10% inoculum to stand at 30° C. for fermentation, and weighed every 12 h. The fermentation is over when the weight loss is less than 1 g for twice. 100 mL of mash after the fermentation was taken and added with 100 mL of water, and 100 mL of liquor sample was steamed out.

5) determination of fermentation performance indicators including $CO_2$ cumulative emission, alcohol content and residual reducing sugars in the liquor sample.

Results are shown in Table 1. No significant difference was observed in the alcohol content and residual sugar content after fermentation with the recombinant strain PGAe, PGA2Ae and PGA2AeΔPor2 compared with the original strain, and no adverse impact on the essential fermentation performance was found after the knockout or overexpression of genes in the present example.

TABLE 1

Determination of fermentation performance by the original strain and the recombinant strains

| Strain | $CO_2$ Weight Loss (g) | Residual Sugar (g/L) | Alcohol Content (% vol) |
|---|---|---|---|
| AY14α | 13.5 | 0.451 | 10.5 |
| PGAe | 13.7 | 0.467 | 10.6 |
| PGA2Ae | 13.6 | 0.465 | 10.5 |
| PGA2AeΔPor2 | 13.5 | 0.490 | 10.7 |

Note:
The data shown are the average of results in three parallel experiments.

6) Determination of yield of esters and alcohols by gas chromatography

Gas Chromatograph: Agilent 7890C; Chromatographic column: special column for Baijiu, AT.LZP-930, 230° C., 50 m×320 μm×1 μm; Detector: Flame Ionization Detector (FID), detector temperature: 200° C.; Carrier gas: high-purity nitrogen, flow rate: 5 mL/min; Detection conditions: programmed temperature increase, stand for 8 min at 50° C. before increasing to 120° C. at a speed of 5° C./min, stand for 8 min; inlet temperature: 200° C.; injection volume: 1.0 μL; split flow mode: split, split ratio: 10:1.

TABLE 2 yield of higher alcohols and esters by the original strain and the recombinant strains (unit: mg/L)

| Strains | ethyl acetate (mg/L) | isoamyl acetate (mg/L) | isoamyl acetate/ethyl acetate | isoamyl alcohol (mg/L) | isobutyl acetate (mg/L) | isobutanol (mg/L) |
|---|---|---|---|---|---|---|
| AY14α | 6.34 ± 0.5 | — | — | 142.33 ± 3.18 | — | 28.97 ± 0.51 |
| PGAe | 1374.54 ± 117.09 | 30.21 ± 0.34 | 0.022 | 50.01 ± 1.43 | — | 12.32 ± 0.41 |
| PGA2Ae | 1425.85 ± 50.73 | 25.00 ± 0.82 | 0.018 | 47.75 ± 0.59 | — | 18.29 ± 0.60 |
| PGA2AeΔPor2 | 1651.89 ± 48.72 | 26.55 ± 2.21 | 0.016 | 42.90 ± 1.88 | — | 24.88 ± 0.49 |

The yield of esters and alcohols in the liquor sample determined by the above-mentioned method is shown in Table 2. It can be seen that the yield of ethyl acetate of the original strain was 6.34 mg/L, increasing to 1374.54 mg/L (216.8 times that of the original strain) after the integration and overexpression of the acetaldehyde dehydrogenase gene ALD6, the acetyl-CoA synthase gene ACS1 and the alcohol acyltransferase gene AeAT9. Further increasing to 1425.85 mg/L (224.9 times that of the original strain) after a further integration and overexpression of the alcohol dehydrogenase gene ADH; and finally reaching 1651.89 mg/L (260.55 times that of the original strain) after a further knockout of the gene POR2. In addition, the yield of isoamyl acetate was very low, the ratio of which to ethyl acetate is almost 0, and no isobutyl acetate was detected. Meanwhile, the content of higher alcohols, especially of isoamyl alcohol, dropped significantly.

Embodiment 3: Experiment of Soy-Flavor Baijiu (Zhaijiu) Fermentation with Strain PGA2AeΔPor2

Soy-flavor Baijiu is produced by fermentation with rice as raw material, Da Qu (prepared by rice, soybean, desmos leaves and Xiaoqu) as saccharifying & fermenting agent. The fermentation process comprises: cooking the rice, adding ground Da Qu (20-24% of raw material) to the cooled rice, followed by adding water, leading to simultaneous saccharification and fermentation instead of solid saccharification. The alcohol content of mature mash could be 12-14 degrees, and a low-alcohol liquor with an alcohol content of 28-38 degrees, commonly known as Zhaijiu, is produced by the kettle distillation method, After being stored, settled and clarified for 7-10 days, Zhaijiu will be soaked in large tanks containing aged fatty pork for about one month before it is extracted, aged, blended, and filtered to obtain finished products of various specifications. Soy-flavor Baijiu, famous for its outstanding soy aroma, originates from the Pearl River Delta of China and has unique Southern China characteristics. Representative products of this type of Baijiu include Yuk Ping Shu, Red-rice Chiew and Kiu Kiang Shuang Jin Chiew. This type of Baijiu is popular among people from all walks of life because of its unique fragrance of rice and fermented soybeans, its noble body as pure as jade and as clean as ice, and its soft, sweet and smooth taste. Soy-flavor Baijiu has development by leaps and bounds as a result of its unique flavor and special production process. The main esters in soy-flavor Baijiu are ethyl lactate and ethyl acetate, which together account for over 95% of the total content of esters. However, the fast ethanol fermentation and high temperature during fermentation process of soy-flavor Baijiu among other factors have an adverse impact on the metabolism of esters, resulting in low levels of ethyl acetate and ethyl lactate in soy-flavor Baijiu, which in turn makes the liquor bland and affects the stability and improvement of its quality. The present example applied the constructed new-type ethyl acetate-producing *Saccharomyces cerevisiae* strain in the fermentation process of soy-flavor Baijiu in order to further increase the content of ethyl acetate in soy-flavor Baijiu and hence fortify the stability of its quality.

1. Method
1) Strains
PGA2AeΔPor2 MY-15 (CGMCC NO. 5635) and H-1 (*Hansenula anomala*, CICC NO. 1312)
2) Fermentation systems: 105 g of cooked rice and 9 g of Daqu were added in a 250 mL Erlenmeyer flask, *Saccharomyces cerevisiae* (1,000,000/mL) was inoculated for the experimental group and no inoculation for the control group; next, water was then added to make it 240 g in total for the fermentation system; the flasks were sealed with plastic film, and three holes were pierced in the plastic film with a syringe; samples in 6, 9, 12, and 15 days of fermentation were taken to determine the essential fermentation performance and the content of esters and higher alcohols.

2. Results and Discussion
Experiment was carried out to investigate soy-flavor Baijiu fermentation with yeast strains. Samples were taken in specific time intervals to determine the alcohol content in each fermentation system. Results are shown in FIG. 7, demonstrating obvious changes in the alcohol content with different yeast strains with time: the alcohol content reached its highest, 13.30 degrees, on day 12 in the control group; peak was reached on day 12 as well for the PGA2AeΔPor2 strain, i.e., 13.60 degrees; the alcohol content increased to its maximum, 13.30 degrees on day 6 and then gradually decreased with time for strain MY-15; and for strain H-1, no obvious changes were observed in alcohol content during the early stage of fermentation, but the alcohol content dropped to 11.10 degrees on day 15. As shown in Table 3, the content of residual reducing sugars all dropped significantly on day 9 compared to that on day 6 for all 3 strains.

TABLE 3 changes of residual reducing sugars with time

| Time (d) | Blank | PGA2AeΔPor2 | MY-15 | H-1 |
|---|---|---|---|---|
| 6 | 2.23 | 1.83 | 1.85 | 1.85 |
| 9 | 1.70 | 1.40 | 1.48 | 1.65 |
| 12 | 1.30 | 1.30 | 1.55 | 1.50 |
| 15 | 1.75 | 1.40 | 1.60 | 1.25 |

FIG. 8 shows the changes in content of ethyl acetate and ethyl lactate with fermentation time in the Zhaijiu fermentation systems with added PGA2AeΔPor2, MY-15 and H-1 strains. The content of ethyl acetate ((A) in FIG. 8) reached its peak 534.43 mg/L, on day 9 for strain PGA2AeΔPor2, and reached its peak 343.8 mg/L and 50.14 mg/L on day 6 for strains My-15 and H-1, correspondingly; the maximum content of ethyl acetate for the control group is 60.1 mg/L and there were no obvious changes in the yield of ethyl acetate with time; in general, strain PGA2AeΔPor2 had the highest yield of ethyl acetate: the yield on day 9 was 8.89 times that of the control group, 1.55 times that of the strain My-15, and 10.66 times that of strain H-1.

Although the yield of ethyl acetate reached its peak on day 9 in the fermentation systems with inoculated strain PGA2AeΔPor2, the yield of ethyl lactate was relatively low. In order to increase the yield of ethyl lactate, the fermentation was extended to 15 d, and the yield of ethyl lactate with time is shown in (B) in FIG. 8. It is demonstrated that all systems showed a gradual increase in the yield of ethyl lactate with the extension of fermentation, which is a result of the accumulation of lactic acid. The content of ethyl lactate reached its peak, 47.69 mg/L, on day 15 d in the fermentation system of PGA2AeΔPor2, which decreased by 45.55% and 35.43% compared with the control and the H-1 strain, correspondingly, and increased by 2.37 times compared with strain My-15. It is demonstrated that the PGA2AeΔPor2 strain of *Saccharomyces cerevisiae* constructed in the present disclosure has a minor impact on the synthesis of ethyl lactate compared to strain MY-15, although there was a decrease compared to the control group. The content of ethyl lactate in soy-flavor Baijiu is generally required to be in the range of 50-1560 mg/L. According to the result of Zhaijiu fermentation with the strain of the present disclosure, the content of ethyl lactate is already quite close to the requirement for soy-flavor Baijiu on day 15. Further optimization of the fermentation process can improve the level of ethyl lactate while maintaining the high capacity of ethyl acetate synthesis.

The changes in levels of various higher alcohols with time were also determined in each fermentation systems as shown in Table 4. The yield of isobutanol, isoamyl alcohol and n-propanol all featured an increase followed by a decrease for strain PGA2AeΔPor2, wherein at the peak of ethyl acetate yield, namely day 9, the content of these higher alcohols were 139.77, 180.9, and 51.57 mg/L, respectively, which were significantly reduced by 53.9%, 59.37%, and 26.69%, respectively, compared with the blank control.

The levels of various higher alcohols all reached theirs minimum values on day 15 for the yeast strains PGA2AeΔPor2, MY-15 and H-1. The isobutanol yields of the three yeast strains were 109.49, 124.58, and 132.79 mg/L respectively, which were reduced by 76.13%, 54.80%, and 45.23% compared with the blank control; the isoamyl alcohol yields were 136.18, 156.33, and 139.29 mg/L, respectively and decreased by 41.61%, 23.36% and 38.45%, respectively, compared with the blank control; the yields of n-propanol were 38.7, 47.42 and 39.03 mg/L, respectively, which means there was barely any difference between the MY-15 strain and the blank control, while the yields of n-propanol dropped by 23.85% and 22.80% in the systems of strain PGA2AeΔPor2 and H-1 compared to the blank control. Similarly, the content of total higher alcohols in the system of strain PGA2AeΔPor2 dropped to 284.37 mg/L on day 15 (Table 4), which is 34.42% less than the control, 13.39% less than My-15, and 8.60% less than H-1. In general, the *Saccharomyces cerevisiae* strain PGA2AeΔPor2 constructed in the present disclosure not only has the capacity in high yield of ethyl acetate, but also has the capacity of reducing yield of higher alcohols.

TABLE 4

Changes in total content of higher alcohols with time

| Time (d) | Blank | PGA2AeΔPor2 | MY-15 | H-1 |
|---|---|---|---|---|
| 6 | 439.56 | 337.28 | 347.52 | 391.29 |
| 9 | 489.54 | 372.23 | 352.95 | 400.56 |
| 12 | 430.27 | 376.00 | 372.47 | 382.53 |
| 15 | 433.62 | 284.37 | 328.33 | 311.11 |

Embodiment 4: Experiment of Second Fermentation of Light-Flavor Baijiu with Strain PGA2AeΔPor2

Light-flavor Baijiu is one of China's three types of flavor Baijiu, featuring an elegant and coordinated fragrance, a gentle sweetness, a full body, a clean and lasting base note. The level of ethyl acetate, one of the featured aroma ingredients of light-flavor Baijiu, determines the quality and style of light-flavor Baijiu. Generally a second fermentation is carried out in the production of light-flavor Baijiu in order to make full use of the remaining starch in the fermented distillers grains, reduce the yield of higher alcohols, and improve the quality of the finished liquor. The pure mash culture in the second fermentation not only produces aroma and alcohol with starch, but also avoids the introduction of miscellaneous flavors of the raw and auxiliary materials into the liquor, contributing to a refreshing distilled spirit. The constructed new-type ethyl acetate-producing *Saccharomyces cerevisiae* strain was applied in the second fermentation of Laobaigan in this example, in order to further increase the yield of ethyl acetate in light-flavour Baijiu and consequently further improving the stability of finished product quality.

1. Method
Strains:
PGA2AeΔPor2, activated Angel Yeast ADY and MY-15
Fermentation Systems:
A second fermentation was carried out in this example using the distillers grains of the first fermentation as the medium, where the content of the residual starch was 17.72 g/100 g of distillers grains. Fermentation was carried out in a 600 mL small jar with a loading capacity of 200 g distillers grains; glucoamylase was added to a level of 0.04 mL/100 g of distillers grains or 4000 U/100 g of distillers grains; the inoculation amount of the control strain ADY was 0.033 g/100 g of distillers grains or 667 million/100 g of distillers grains; the inoculation amount of the yeast strain in the experimental group was 667 million/100 g of distillers grains; the jar was sealed in water and fermentation continued at 30° C. for 10 days.

2. Results and Discussion

TABLE 5

Synthesis of esters after inoculation of each strain (unit: mg/L)

| Strains | ethyl acetate | ethyl lactate | ethyl butyrate | ethyl caproate | Total esters |
|---|---|---|---|---|---|
| ADY | 25.60 | 410.03 | 22.73 | 15.43 | 473.87 |
| PGA2AeΔPor2 | 305.30 | 336.47 | — | 15.73 | 657.47 |
| MY-15 | 148.77 | 474.33 | 28.15 | 15.97 | 657.87 |

Angel yeast strain ADY and strain MY-15 were used as controls. The contents of various flavor compounds in distillers grains of PGA2AeΔPor2 were determined, and the synthesis capability thereof in light-flavour Baijiu was evaluated, as shown in Table 5. It is demonstrated that strain PGA2AeΔPor2 has the highest capacity of ethyl acetate production with an ethyl acetate yield of 305.30 mg/L, which is 11.93 times that of strain ADY and 2.05 times that of strain MY-15. After inoculation of the strain, the yield of ethyl lactate in the fermentation system was relatively low compared with the ADY and MY-15 strains, which were reduced by 17.94% and 29.06%, respectively, indicating that the engineered strain constructed in this disclosure had a greater disturbance on the synthesis of ethyl lactate in the fermentation system. The yield ratio of ethyl acetate and ethyl lactate could be adjusted by further adjusting the fermentation process, such as prolonging the fermentation time. In addition, there was not much significant difference in the level of ethyl caproate in the fermentation systems between this strain and strain ADY and MY-15; it was demonstrated that the constructed strain does not have the capacity of ethyl butyrate synthesis. The yield of total esters was relatively high (657.47 mg/L), which was close to that of strain MY-15, and was 1.39 times that of the control strain ADY.

TABLE 6

Synthesis of higher alcohols after inoculation of each strain (unit: mg/L)

| Strains | n-propanol | isobutanol | isoamyl alcohol | phenyl-ethanol | total higher alcohols |
|---|---|---|---|---|---|
| ADY | 8.80 | 11.70 | 45.07 | 14.53 | 80.10 |
| PGA2AeΔPor2 | 9.07 | 12.17 | 19.40 | 10.33 | 50.97 |
| MY-15 | 15.95 | 14.23 | 42.20 | 19.80 | 86.87 |

The yield of various higher alcohols in the fermentation system after inoculation of each yeast strain was determined, as shown in Table 6. The yield of isoamyl alcohol was 19.40 mg/L in the PGA2AeΔPor2 fermentation system, showing a most obvious decrease compared to the control groups: 56.96% lower than that of strain ADY and 54.03% lower than that of strain MY-15. The second obvious decrease was in the yield of benzenediol, 10.33 mg/L, which was 28.91% lower than that of control strain ADY and 47.83% lower than that of strain MY-15. The total yield of higher alcohols was 50.97 mg/L, which was 36.37% lower than that of the control strain ADY and 41.33% lower than that of MY-15.

In general, the yield of various higher alcohols and total higher alcohols increased in the system of strain MY-15 and ADY, except for the yield of isoamyl alcohol which slightly decreased. On the contrary, the constructed strain PGA2AeΔPor2 in the present disclosure provided for a more obvious reduction effect of higher alcohols yield.

TABLE 7

Physical and chemical indexes of fermented grains

| Strains | acidity (mmol/ 10 g distillers grains) | Residual starch g/100 g distillers grain | water % | alcohol content % (V/V) |
|---|---|---|---|---|
| ADY | 1.76 | 9.67 | 66.43 | 5.90 |
| PGA2AeΔPor2 | 2.22 | 9.82 | 68.00 | 7.10 |
| MY-15 | 1.74 | 8.97 | 67.90 | 7.03 |

Next, the physical and chemical indexes of the fermented grains were detected, as shown in Table 7. It can be seen that the alcohol content in the fermentation system of strain PGA2AeΔPor2 was 7.10 degrees, which is similar to that of strain MY-15, and 16.9% higher than that of the control strain ADY. Moreover, the fermentation system of PGA2AeΔPor2 demonstrated a higher acidity and water content than strain ADY and MY-15. On the whole, compared with the low alcohol content of ADY, strain PGA2AeΔPor2 has a capacity of similar or even slightly higher ethanol fermentation than MY-15 under the high-acidity conditions of the second fermentation of light-flavor Baijiu (reflected in alcohol content and residual starch content); consequently the goal is achieved to improve the synthesis capacity of ethyl acetate while reducing the yield of higher alcohols without affecting the essential fermentation performance like alcohol yield.

What is claimed is:

1. A genetically engineered strain of *Saccharomyces cerevisiae*, wherein, the engineered strain heterologous overexpresses an acetaldehyde dehydrogenase gene ALD6, an acetyl-CoA synthase gene ACS1 and an alcohol acyltransferase gene AeAT9; the engineered strain further heterogeneously overexpresses an alcohol dehydrogenase gene ADH2; and the engineered strain does not express a porin gene POR2 responsible for transporting cytosolic pyruvate into the mitochondria.

2. The genetically engineered strain of *Saccharomyces cerevisiae* according to claim 1, wherein, the acetaldehyde dehydrogenase gene ALD6 has the nucleotide sequence as shown in SEQ ID NO: 1; and/or the acetyl-CoA synthase gene ACS1 has the nucleotide sequence as shown in SEQ ID NO:2; and/or the alcohol dehydrogenase gene ADH2 has the nucleotide sequence as shown in SEQ ID NO:3; and/or the alcohol acyltransferase gene AeAT9 has the nucleotide sequence as shown in SEQ ID NO:4; and/or the porin gene POR2 responsible for transporting cytosolic pyruvate into the mitochondria has the nucleotide sequence as shown in SEQ ID NO:5.

3. The genetically engineered strain of *Saccharomyces cerevisiae* according to claim 1, wherein, the acetaldehyde dehydrogenase gene ALD6 is connected to a strong promoter PGK1$_P$ (SEQ ID NO:7) and a terminator GIC1$_T$ (SEQ ID NO:8); and/or the acetyl-CoA synthetase gene ACS1 is connected to a strong promoter TEF1$_P$ (SEQ ID NO:9) and a terminator PGK1$_T$ (SEQ ID NO:10); and/or the alcohol acyltransferase gene AeAT9 is connected to a strong promoter PGK1$_P$ (SEQ ID NO:7) and a terminator PGK1$_T$ (SEQ ID NO:10); and/or the alcohol dehydrogenase gene ADH2 is connected to an inducible promoter HTX7$_P$ (SEQ ID NO:11) and a terminator PGK1$_T$ (SEQ ID NO:10).

4. The genetically engineered strain of *Saccharomyces cerevisiae* according to claim 2, wherein, the acetaldehyde dehydrogenase gene ALD6 is connected to a strong promoter PGK1$_P$ (SEQ ID NO:7) and a terminator GIC1$_T$ (SEQ ID NO:8); and/or the acetyl-CoA synthetase gene ACS1 is connected to a strong promoter TEF1$_P$ (SEQ ID NO:9) and a terminator PGK1$_T$ (SEQ ID NO:10); and/or the alcohol acyltransferase gene AeAT9 is connected to a strong promoter PGK1$_P$ (SEQ ID NO:7) and a terminator PGK1$_T$ (SEQ ID NO:10); and/or the alcohol dehydrogenase gene ADH2 is connected to an inducible promoter HTX7$_P$ (SEQ ID NO:11) and a terminator PGK1$_T$ (SEQ ID NO:10).

5. The genetically engineered strain of *Saccharomyces cerevisiae* according to claim 1, wherein, an original strain of the engineered strain is *Saccharomyces cerevisiae* CICC32315.

6. The genetically engineered strain of *Saccharomyces cerevisiae* according to claim 2, wherein, an original strain of the engineered strain is *Saccharomyces cerevisiae* CICC32315.

7. The genetically engineered strain of *Saccharomyces cerevisiae* according to claim 3, wherein, an original strain of the engineered strain is *Saccharomyces cerevisiae* CICC32315.

8. The genetically engineered strain of *Saccharomyces cerevisiae* according to claim 4, wherein, an original strain of the engineered strain is *Saccharomyces cerevisiae* CICC32315.

9. The genetically engineered strain of *Saccharomyces cerevisiae* according to claim 5, wherein, the acetyl-CoA synthetase gene ACS1, the aldehyde dehydrogenase gene ALD6 and the alcohol acyltransferase gene AeAT9 are sequentially connected, inserted into and replace a coding gene Gal80 region of a galactose transcription regulator in the *Saccharomyces cerevisiae*; the coding gene Gal80 has the nucleotide sequence as shown in SEQ ID NO:6.

10. The genetically engineered strain of *Saccharomyces cerevisiae* according to claim 6, wherein, the acetyl-CoA synthetase gene ACS1, the aldehyde dehydrogenase gene ALD6 and the alcohol acyltransferase gene AeAT9 are sequentially connected, inserted into and replace a coding gene Gal80 region of a galactose transcription regulator in the *Saccharomyces cerevisiae*; the coding gene Gal80 has the nucleotide sequence as shown in SEQ ID NO:6.

11. The genetically engineered strain of *Saccharomyces cerevisiae* according to claim 7, wherein, the acetyl-CoA synthetase gene ACS1, the aldehyde dehydrogenase gene ALD6 and the alcohol acyltransferase gene AeAT9 are sequentially connected, inserted into and replace a coding gene Gal80 region of a galactose transcription regulator in the *Saccharomyces cerevisiae*: the coding gene Gal80 has the nucleotide sequence as shown in SEQ ID NO:6.

12. The genetically engineered strain of *Saccharomyces cerevisiae* according to claim 8, wherein, the acetyl-CoA synthetase gene ACS1, the aldehyde dehydrogenase gene ALD6 and the alcohol acyltransferase gene AeAT9 are sequentially connected, inserted into and replace a coding gene Gal80 region of a galactose transcription regulator in the *Saccharomyces cerevisiae*; the coding gene Gal80 has the nucleotide sequence as shown in SEQ ID NO:6.

13. The genetically engineered strain of *Saccharomyces cerevisiae* according to claim 5, wherein, the alcohol dehydrogenase gene ADH2 is inserted at a site of, and replaces an isoamyl acetate hydrogenase gene IAH1; the isoamyl acetate hydrogenase gene IAH1 has the nucleotide sequence as shown in SEQ ID NO:12.

14. The genetically engineered strain of *Saccharomyces cerevisiae* according to claim 6, wherein, the alcohol dehydrogenase gene ADH2 is inserted at a site of, and replaces an isoamyl acetate hydrogenase gene IAH1; the isoamyl acetate hydrogenase gene IAH1 has the nucleotide sequence as shown in SEQ ID NO:12.

15. The genetically engineered strain of *Saccharomyces cerevisiae* according to claim 7, wherein, the alcohol dehydrogenase gene ADH2 is inserted at a site of, and replaces an isoamyl acetate hydrogenase gene IAH1; the isoamyl acetate hydrogenase gene IAH1 has the nucleotide sequence as shown in SEQ ID NO:12.

16. The genetically engineered strain of *Saccharomyces cerevisiae* according to claim 8, wherein, the alcohol dehydrogenase gene ADH2 is inserted at a site of, and replaces an isoamyl acetate hydrogenase gene IAH1; the isoamyl acetate hydrogenase gene IAH1 has the nucleotide sequence as shown in SEQ ID NO:12.

17. The genetically engineered strain of *Saccharomyces cerevisiae* according to claim 1, wherein, the porin gene POR2 responsible for transporting cytosolic pyruvate into the mitochondria is knocked out.

18. A method for constructing the genetically engineered strain of *Saccharomyces cerevisiae* according to claim 1, comprising: introducing into *Saccharomyces cerevisiae* the aldehyde dehydrogenase gene ALD6, the acetyl-CoA synthase gene ACS1, the alcohol acyltransferase gene AeAT9 and the alcohol dehydrogenase gene ADH2; and inactivating or knocking out the porin gene POR2 responsible for transporting cytosolic pyruvate into the mitochondria.

19. The method according to claim 18, further comprising:
  (1) obtaining a first recombinant strain through introducing the acetyl-CoA synthetase gene ACS1, the aldehyde dehydrogenase gene ALD6 and the alcohol acyltransferase gene AeAT9 into the *Saccharomyces cerevisiae*, and replacing the coding gene Gal80 of the transcriptional regulator of galactose in *Saccharomyces cerevisiae* by homologous recombination;
  (2) obtaining a second recombinant strain through introducing the alcohol dehydrogenase gene ADH2 into the first recombinant strain, and replacing the isoamyl acetate hydrogenase gene IAH1 in *Saccharomyces cerevisiae* by homologous recombination; and
  (3) knocking out the porin gene POR2 responsible for transporting cytosolic pyruvate into the mitochondria in the second recombinant strain to obtain the genetically engineered strain of *Saccharomyces cerevisiae*; the knockout of the porin gene POR2 is realized by homologous recombination of POR2 and a KanMX resistance gene.

20. A method for brewing by fermentation, comprising the step of culturing the genetically engineered strain of *Saccharomyces cerevisiae* according to claim 1 in a liquid medium.

* * * * *